United States Patent
Choi et al.

(10) Patent No.: US 12,268,524 B2
(45) Date of Patent: Apr. 8, 2025

(54) ELECTRONIC DEVICE PROVIDING CONTACT PRESSURE INFORMATION AND METHOD FOR CONTROLLING THE SAME

(71) Applicant: SAMSUNG ELECTRONICS CO., LTD., Suwon-si (KR)

(72) Inventors: Yoonhee Choi, Suwon-si (KR); Hyoungseon Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 244 days.

(21) Appl. No.: 17/375,407

(22) Filed: Jul. 14, 2021

(65) Prior Publication Data

US 2022/0015706 A1 Jan. 20, 2022

(30) Foreign Application Priority Data

Jul. 15, 2020 (KR) .......................... 10-2020-0087846

(51) Int. Cl.
*A61B 5/00* (2006.01)

(52) U.S. Cl.
CPC .......... *A61B 5/6843* (2013.01); *A61B 5/0077* (2013.01); *A61B 5/441* (2013.01); *A61B 5/684* (2013.01); *A61B 5/743* (2013.01)

(58) Field of Classification Search
None
See application file for complete search history.

(56) References Cited

U.S. PATENT DOCUMENTS

| | | |
|---|---|---|
| 2008/0012582 A1 | 1/2008 | Jang et al. |
| 2016/0193108 A1 | 7/2016 | Cho |
| 2017/0367471 A1* | 12/2017 | Straka ................ A46B 15/0044 |
| 2018/0357761 A1* | 12/2018 | Shen ....................... A61B 5/441 |
| 2018/0368701 A1* | 12/2018 | Vule ..................... A61B 5/0205 |
| 2019/0191850 A1* | 6/2019 | Yoganandan ....... B26B 21/4056 |
| 2019/0357779 A1* | 11/2019 | Park ....................... A61B 5/746 |
| 2021/0201194 A1* | 7/2021 | Masculo ................ G16H 40/40 |
| 2022/0225927 A1* | 7/2022 | Yoo ........................ A61B 5/441 |

FOREIGN PATENT DOCUMENTS

| | | |
|---|---|---|
| CN | 110882028 | 3/2020 |
| JP | 2008-054890 | 3/2008 |
| KR | 10-0756409 | 9/2007 |
| KR | 10-2009-0124140 | 12/2009 |
| KR | 10-2019-0096574 | 8/2019 |

OTHER PUBLICATIONS

International Search Report and Written Opinion dated Oct. 21, 2021 in corresponding International Application No. PCT/KR2021/009062.

* cited by examiner

*Primary Examiner* — Rene T Towa
*Assistant Examiner* — Matthew Eric Ogles
(74) *Attorney, Agent, or Firm* — Nixon & Vanderhye, P.C.

(57) ABSTRACT

Disclosed are an electronic device for providing contact pressure information and a method for controlling the electronic device. According to an embodiment, an electronic device comprises: a display, a camera, a communication circuit, and at least one processor configured to: control the communication circuit to establish a communication channel with an external electronic device via the communication circuit, obtain data for a contact pressure value from the external electronic device via the established communication channel, and output information related to the contact pressure value via the display using the obtained data for the contact pressure value.

12 Claims, 27 Drawing Sheets

ELECTRONIC DEVICE PROVIDING CONTACT PRESSURE INFORMATION AND METHOD FOR CONTROLLING THE SAME

CROSS-REFERENCE TO RELATED APPLICATION

This application is based on and claims priority under 35 U.S.C. § 119 to Korean Patent Application No. 10-2020-0087846, filed on Jul. 15, 2020, in the Korean Intellectual Property Office, the disclosure of which is incorporated by reference herein in its entirety.

BACKGROUND

Field

The disclosure relates to an electronic device providing contact pressure information and a method for controlling the electronic device.

Description of Related Art

More and more services and additional functions are being provided via electronic devices, e.g., smart mirrors. For example, a user may carry out diagnosis on users skin via an electronic device, e.g., a smart mirror. As such, steadily increasing demand for home skin diagnosis and beauty devices calls for technology for skin condition measurement or skincare.

In order to measure the skin condition, e.g., the content of moisture or oil of the skin or the elasticity of the skin, the pressure at which the skin condition measuring device contacts the skin needs to remain constant. For example, when the moisture content of the skin is measured, the measurement of skin impedance may be varied depending on the contact pressure. Thus, a failure to maintain a proper contact pressure may cause a result from the actual content of skin moisture. Further, the skin condition measurement or skincare may remain reliable when it is carried out at the same or similar contact pressure to the previous contact pressure, i.e., at a constant contact pressure. In recent years, as ordinary consumers, who are not skincare professionals, use a skin condition measuring device or a skincare device, there is a need for developing technology capable of increasing the reliability of skin condition measurement or skincare.

The above information is presented as background information only to assist with an understanding of the disclosure. No determination has been made, and no assertion is made, as to whether any of the above might be applicable as prior art with regard to the disclosure.

SUMMARY

Embodiments of the disclosure proved an electronic device which allows non-professional, ordinary consumers to obtain constant skin condition measurement results or skincare results by providing information related to a proper contact pressure in carrying out skin condition measurement or skincare.

Embodiments of the disclosure provide an electronic device which allows non-professional, ordinary consumers to obtain constant skin condition measurement results or skincare results by providing information about a recommended path and recommended contact pressure for skin condition measurement or skincare.

Embodiments of the disclosure provide a method for operating an electronic device which allows non-professional, ordinary consumers to obtain constant skin condition measurement results or skincare results by providing information related to a proper contact pressure in carrying out skin condition measurement or skincare.

Embodiments of the disclosure provide a method for operating an electronic device which allows non-professional, ordinary consumers to obtain constant skin condition measurement results or skincare results by providing information about a recommended path and recommended contact pressure for skin condition measurement or skincare.

In accordance with an example embodiment, an electronic device comprises: a display, a camera, a communication circuit, and at least one processor configured to: control the communication circuit to establish a communication channel with an external electronic device via the communication circuit, obtain information for identifying a type of the external electronic device from the external electronic device via the established communication channel, based on the type of the external electronic device identified using the obtained information being a skin contact device, identifying a first point where the external electronic device is positioned on a user's body portion using the camera, obtain information about a contact pressure value from the external electronic device via the established communication channel, and output information related to a current contact pressure value for the first point via the display.

In accordance with an example embodiment, a method for controlling an electronic device comprises: controlling a communication circuit of the electronic device to establish a communication channel with an external electronic device via the communication circuit, obtaining information for identifying a type of the external electronic device from the external electronic device via the established communication channel, based on the type of the external electronic device identified using the obtained information being a skin contact device, identifying a first point where the external electronic device is positioned on a user's body portion using a camera of the electronic device, obtaining information about a contact pressure value from the external electronic device via the established communication channel, and outputting information related to a current contact pressure value for the first point via a display of the electronic device.

Other aspects, advantages, and salient features of the disclosure will become apparent to those skilled in the art from the following detailed description, which, taken in conjunction with the annexed drawings, discloses example embodiments of the disclosure.

BRIEF DESCRIPTION OF THE DRAWINGS

The above and other aspects, features and advantages of certain embodiments of the present disclosure will be more apparent from the following detailed description, taken in conjunction with the accompanying drawings, in which.

Throughout the drawings, like reference numerals will be understood to refer to like parts, components, and structures.

DETAILED DESCRIPTION

Figure 1A:
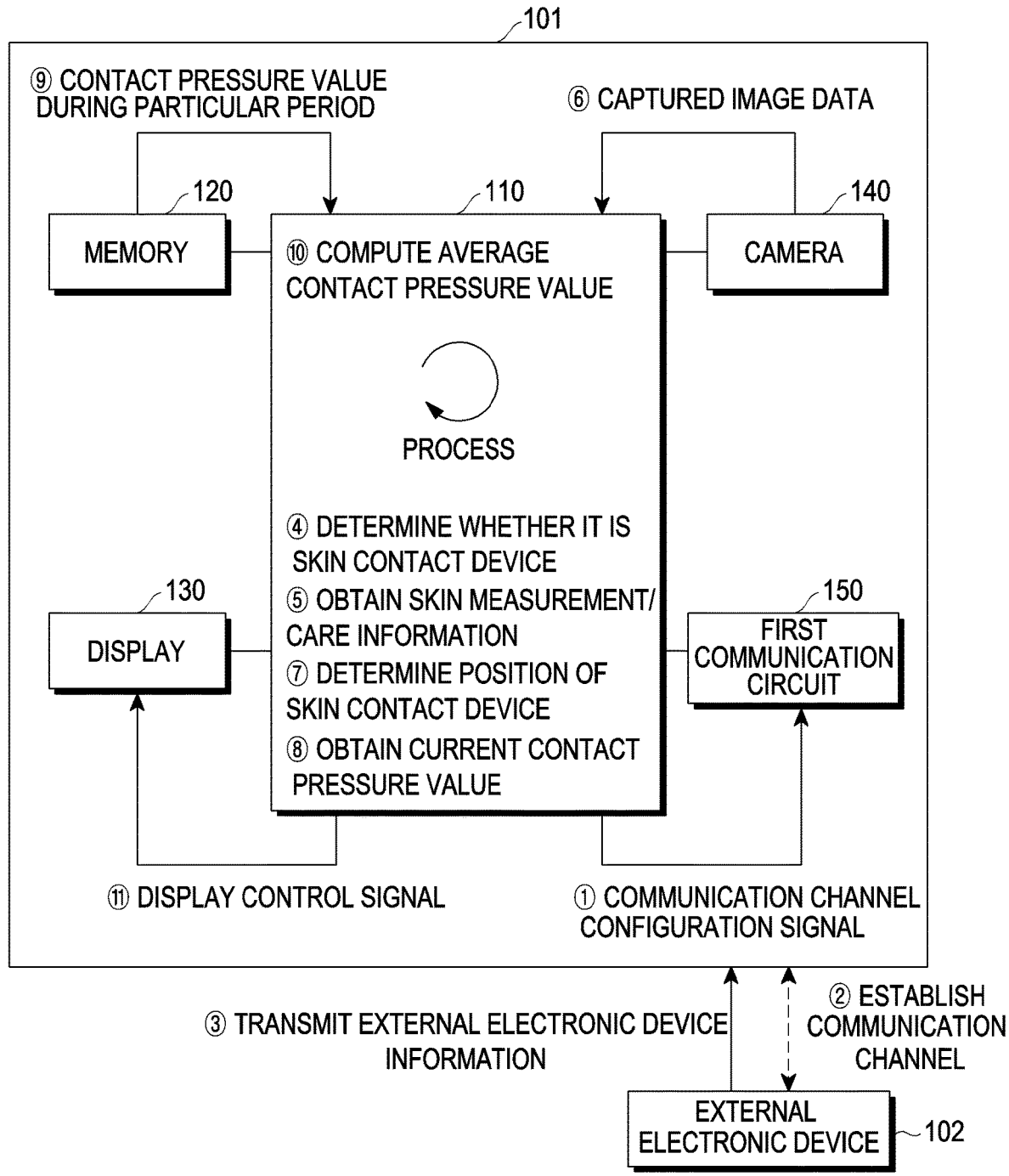
FIG. 1A is a diagram illustrating an example electronic device according to various embodiments.

FIG. 1A is a diagram illustrating an example electronic device 101 according to various embodiments.

Referring to FIG. 1A, according to an embodiment, an electronic device 101 may include a processor (e.g., including processing circuitry) 110, a memory 120, a display 130, a camera 140, and a first communication circuit 150. In some embodiments, some of the components may be implemented as single integrated circuitry. For example, the camera 140 may be embedded in the display 130. According to an embodiment, at least some of the components of FIG. 1 may be excluded from the electronic device 101.

According to an embodiment, the processor 110 may include various processing circuitry and execute, for example, software (e.g., a program) to control at least one other component (e.g., a hardware or software component) of the electronic device 101 coupled with the processor 110, and may perform various data processing or computation. According to an embodiment, as at least part of the data processing or computation, the processor 110 may load a command or data obtained from another component (e.g., the sensor module 176) in the memory 120, process the command or the data stored in the memory 120, and store resulting data in the memory 120. According to an embodiment, the processor 110 may include, for example and without limitation, a main processor (e.g., a central processing unit (CPU) or an application processor (AP)), and an auxiliary processor (e.g., a graphics processing unit (GPU), an image signal processor (ISP), a sensor hub processor, a communication processor (CP)), or the like, that is operable independently from, or in conjunction with, the main processor. The auxiliary processor may be adapted to consume less power than the main processor, or to be specific to a specified function. According to an embodiment, the auxiliary processor may be implemented as separate from, or as part of the main processor. The auxiliary processor may control at least some of functions or states related to at least one component (e.g., the display 130 or the camera 140) of the electronic device 101, instead of the main processor while the main processor is in an inactive (e.g., sleep) state or along with the main processor while the main processor is an active state (e.g., executing an application). According to an embodiment, the auxiliary processor (e.g., an image signal processor) may be implemented as part of another component (e.g., the camera 140) functionally related thereto.

According to an embodiment, the processor 110 may control the communication circuit 150 to establish a communication channel with an external electronic device 102 via the communication circuit 150 (① and ② of FIG. 1A). According to an embodiment, the communication channel may include a wired communication channel or a wireless communication channel. According to an embodiment, the wired communication channel may include, e.g., a local area network (LAN) communication channel or a power line communication channel. According to an embodiment, the wireless communication channel may include, e.g., a short-range communication network communication channel, such as Bluetooth, Wi-Fi direct, or infrared data association (IrDA), or a long-range communication network communication channel, such as cellular network, Internet, or computer network (e.g., LAN or wide area network (WAN)).

According to an embodiment, the processor 110 may obtain device information about the external electronic device 102 using the communication channel established with the external electronic device 102 (③ of FIG. 1A). According to an embodiment, the device information about the external electronic device 102 may include at least one of, e.g., information for identifying the type of the external electronic device 102 (e.g., whether the external electronic device 102 is a skin contact device or another type of device), information about the device model name of the external electronic device 102, information about the function supported by the external electronic device 102, information about the shape of the external electronic device 102, or the like. According to an embodiment, the device information about the external electronic device 102 may be transmitted to the electronic device 101 via a specific format of data frame. According to an embodiment, the data frame may refer, for example, to a unit of information which is configured and transmitted as at least one block or at least one packet over a data communication network where devices (e.g., the electronic device 101 and the external electronic device 102) are connected with one another.

According to an embodiment, the processor 110 may identify whether the type of the external electronic device 102 is a skin contact device using the information obtained from the external electronic device 102 (④ of FIG. 1A). According to an embodiment, the processor 110 may parse a specific format of frame obtained from the external electronic device 102 and identify data (e.g., information for identifying the type of the external electronic device 102) included in the specific format of frame, thereby identifying whether the type of the external electronic device 102 is a skin contact device.

According to an embodiment, when the type of the external electronic device 102 is a skin contact device, the processor 110 may obtain skin measurement/care information from the external electronic device 102 (⑤ of FIG. 1A). According to an embodiment, the processor 110 may request the external electronic device 102 to provide skin measurement/care information via the first communication circuit 150. According to an embodiment, the skin measurement/care information may include at least one of information about a recommended measurement position (e.g., a specific point) for performing skin condition measurement or skincare, information about per-part or each part (e.g., the left cheek, right cheek, around the chin, and/or the forehead) proper contact pressure value of the user's body portion (e.g., the face), or information about a recommended measurement path for performing skin condition measurement or skincare. According to an embodiment, the skin measurement/care information may be obtained from a server operably connected with the electronic device 101.

According to an embodiment, the processor 110 may identify the point where the external electronic device 102 is positioned (e.g., in contact or adjacent to) on the user's face (⑦ of FIG. 1A). According to an embodiment, the processor 110 may identify the shape of the external electronic device 102 using the camera 140 (⑥ of FIG. 1A). According to an embodiment, the processor 110 may identify the shape of a front end of the external electronic device 102 that contacts the user's skin from the identified shape of the external electronic device 102, using the shape of the external electronic device 102 received from the external electronic device 102. According to an embodiment, the processor 110 may identify the shape of the front end of the external electronic device 102 by recognizing the color of the front end of the external electronic device 102 and a designated marker on the front end of the external electronic device 102. According to an embodiment, the processor 110 may identify the point where the front end shape of the external electronic device 102 is positioned on the user's skin (e.g., face). According to an embodiment, the processor 110 may identify the point where the external electronic device 102 is positioned on the user's body portion (e.g., face) by identifying the point where the front end shape is positioned on the user's skin (e.g., face). According to an embodiment, there may be such an occasion where the front end shape of the external electronic device 102 is not correctly identified by the body of the external electronic device 102 or the user's hand holding the external electronic device 102. For example, as at least part of the front end shape of the external electronic device 102 is hidden by the body of the external electronic device 102 or the user's hand holding the external electronic device 102, the front end shape of the external electronic device 102 may not correctly be identified. In this case, according to an embodiment, the processor 110 may determine that a substantial center portion of the user's hand or body of the image of the body of the external electronic device 102 or the image of the user's hand obtained by the camera 140 is the point where the front end of the external electronic device 102 is positioned.

According to an embodiment, the processor 110 may obtain information about the contact pressure value from the external electronic device 102 (⑧ of FIG. 1A). According to an embodiment, the processor 110 may request the external electronic device 102 to provide the information about the contact pressure value via the first communication circuit 150. However, the information about the contact pressure value, according to an embodiment, may be transmitted to the electronic device 101, along with or included in skin measurement/care information if the external electronic device 102 contacts the user's skin. In other words, if a contact of the external electronic device 102 to the user's skin is detected, the information about the contact pressure value, according to an embodiment, may be transmitted from the external electronic device 102 to the electronic device 101 even before performing the operation of identifying the point where the external electronic device 102 is positioned (e.g., in contact or adjacent) on the user's face. According to an embodiment, the information about the contact pressure value may be transmitted to the electronic device 101 automatically without receiving a request from the electronic device 101 if a contact of the external electronic device 102 to the user's skin is detected. According to an embodiment, in the case where the external electronic device 102 contacts the user's skin (e.g., face), the external electronic device 102 may include a pressure sensor for measuring the contact pressure value. According to an embodiment, the external electronic device 102 may obtain the contact pressure value from the pressure sensor when the external electronic device 102 is brought in contact with the user's skin by the user. According to an embodiment, the external electronic device 102 may transmit the obtained information about the contact pressure value to the electronic device 101 via the communication channel.

According to an embodiment, the processor 110 may output contact pressure information related to the current contact pressure value via the display 130, using the obtained information about the contact pressure value (⑪ of FIG. 1A). For example, according to an embodiment, the processor 110 may output relative information (e.g., 5 of values preset to range from 0 to 10) or absolute information (e.g., 10 pascals (Pa)) about the obtained contact pressure value, via the display 130. According to an embodiment, the memory 120 may store a lookup table in which contact pressure ranges and relative values have been mapped to one another, for the processor 110 to determine the relative information. According to an embodiment, the processor 110 may determine the relative information using the lookup table. According to an embodiment, the processor 110 may set the information about the per-part proper pressure value of the user's body portion (e.g., face) received from the external electronic device 102, as a recommended pressure value and output the current contact pressure value and the recommended contact pressure value via the display 130. According to an embodiment, the processor 110 may compare the information about the per-part (e.g., the left cheek, right cheek, around the chin, and/or the forehead) proper contact pressure values of the user's body portion (e.g., face) received from the external electronic device 102 with the obtained contact pressure value, determine whether the current contact pressure value is a proper contact pressure, and output the result of the determination (e.g., proper) via the display 130. According to an embodiment, as illustrated, for example, in FIG. 4D, the processor 110 may output the current contact pressure value measured and contact pressure values for the contacts made during a specific period (e.g., one week) via the display 130. According to an embodiment, the processor 110 may compute (e.g., determine) the average contact pressure value for the contacts made to a specific point (e.g., the right cheek) during a specific period (e.g., one week), stored in the memory 120 (⑨ and ⑩ of FIG. 1A). According to an embodiment, the processor 110 may compare the computed average contact pressure value with the current contact pressure value received from the external electronic device 102. Thus, skin condition measurement or skincare may be performed constantly under the same or similar pressure condition, delivering a reliable result of skin condition measurement or skincare.

According to an embodiment, the memory 120 may store various data used by at least one component (e.g., the processor 110 or the camera 140) of the electronic device 101. The various data may include, for example, software (e.g., the program) and input data or output data for a command related thereto. According to an embodiment, the memory 120 may include a volatile or non-volatile memory. The program may be stored, as software, in the memory and may include, e.g., an operating system (OS), middleware, an application, or the like. According to an embodiment, the memory 120 may store information about the contact pressure value during a specific period, received from the external electronic device 102.

According to an embodiment, the display 130 may visually provide information to the outside (e.g., the user) of the electronic device 101. According to an embodiment, the display 130 may include, for example, a display, a hologram device, or a projector and control circuitry to control a corresponding one of the display, hologram device, and projector. According to an embodiment, the display 130 may include touch circuitry adapted to detect a touch, or sensor circuitry (e.g., a pressure sensor) adapted to measure the intensity of force incurred by the touch. According to an embodiment, the display 130 may obtain a display control signal from the processor 110. According to an embodiment, the display control signal may include at least one of a command for displaying a recommended pressure value for a specific point, a command for displaying a result of determination of whether the current contact pressure value is a proper pressure, or a command for displaying a result of comparison as to how much difference is made between the current contact pressure value measured and the pressure value for the contacts made during a specific period (e.g., one week).

According to an embodiment, the camera 140 may capture a still image or moving image. According to an embodiment, the camera module 180 may include one or more lenses, image sensors (e.g., charge-coupled devices (CCDs), complementary metal-oxide-semiconductors (CMOSs), or the like), image signal processors, flashes, etc.

According to an embodiment, the first communication circuit 150 may establish a direct (e.g., wired) communication channel or a wireless communication channel between the electronic device 101 and the external electronic device 102 or support communication through the established communication channel. According to an embodiment, the first communication circuit 150 may include one or more communication processors that may include various communication processing circuitry and are operable independently from the processor 110 (e.g., the application processor (AP)) and supports a direct (e.g., wired) communication or a wireless communication. According to an embodiment, the first communication circuit 150 may include a wireless communication circuit (e.g., a cellular communication circuit, a short-range wireless communication circuit, or a global navigation satellite system (GNSS) communication circuit) or a wired communication circuit (e.g., a local area network (LAN) communication circuit or a power line communication (PLC) circuit). A corresponding one of these communication circuits may communicate with the external electronic device 102 via the first network (e.g., a short-range communication network, such as Bluetooth™, wireless-fidelity (Wi-Fi) direct, or infrared data association (IrDA)) or the second network (e.g., a long-range communication network, such as a cellular network, the Internet, or a computer network (e.g., LAN or wide area network (WAN)). These various types of communication circuits may be implemented as a single component (e.g., a single chip), or may be implemented as multi components (e.g., multi chips) separate from each other. According to an embodiment, the wireless communication circuit may identify and authenticate the electronic device 101 in a communication network, such as the first network or the second network, using subscriber information (e.g., international mobile subscriber identity (IMSI)) stored in the subscriber identification module.

Figure 1B:
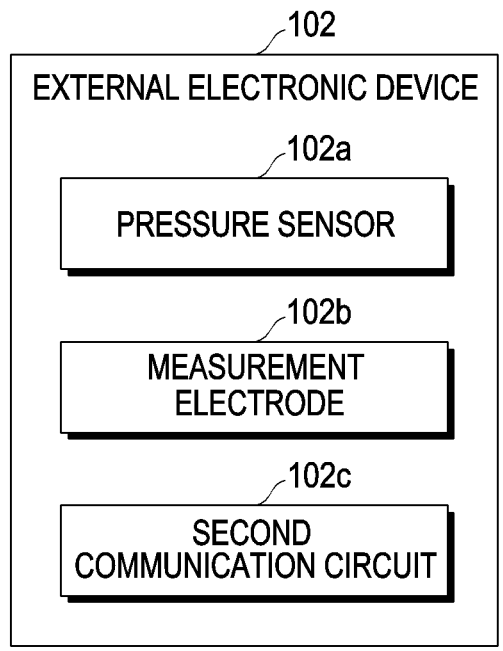
FIGS. 1B, 1C, and 1D diagrams illustrating an example external electronic device according to various embodiments.
Figure 1C:
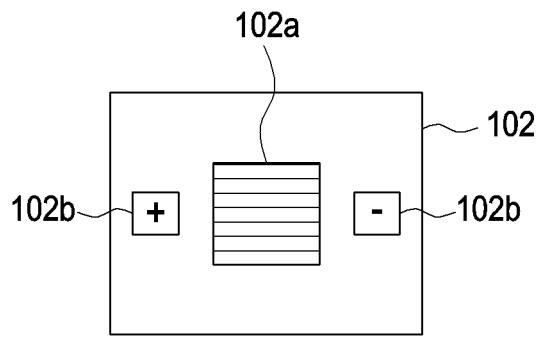
Figure 1D:
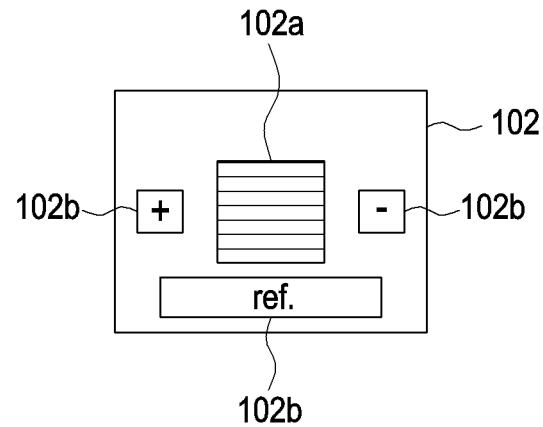

FIGS. 1B, 1C, and 1D are diagrams illustrating an example external electronic device 102 according to various embodiments.

Referring to FIG. 1B, according to an embodiment, an external electronic device 102 may include a pressure sensor 102a, a measurement electrode 102b, and a second communication circuit 102c. According to an embodiment, the pressure sensor 102a may include various circuitry and sense a pressure in a contact state when the external electronic device 102 contacts an external object (e.g., the user's skin). According to an embodiment, the pressure sensor 102a may include, e.g., a force sensitive register (FSR) pressure sensor, a capacitive pressure sensor (CPS), or the like. According to an embodiment, the FSR pressure sensor may include a sensor that measures the contact pressure using variations in the resistance of the sensor according to the pressure. According to an embodiment, the CPS may include a sensor that measures the contact pressure using the principle that capacitance increases as the contact pressure rises. According to an embodiment, the pressure sensor 102a may be placed around the center of a back end of the external electronic device 102 as shown in FIG. 1C. According to an embodiment, the pressure sensor 102a may have a rectangular or circular shape but is not limited thereto. According to an embodiment, the pressure sensor 102a may be disposed to be exposed to the outside of the housing of the external electronic device 102 to come in contact or adjacent to the user's skin. According to an embodiment, the measurement electrode 102b may be configured to input a predetermined frequency of input current to the user's skin and receive a current returning from the skin. According to an embodiment, the measurement electrode 102b may be disposed to be exposed to the outside of the housing of the external electronic device 102 to come in contact or adjacent to the user's skin. According to an embodiment, the measurement electrode 102b may include an input terminal (e.g., a + terminal) configured to provide the input current to the user's skin and a receiving terminal (e.g., a − terminal) configured to receive the current returning from the user's skin, as shown in FIG. 1C. According to an embodiment, the measurement electrode 102b may further include a reference electrode as shown in FIG. 1D. According to an embodiment, the input terminal and the receiving terminal may be distinctly disposed in positions adjacent to each other. According to an embodiment, the pressure sensor 102a and the measurement electrode 102b may be disposed in a front end 210 configured to come in contact or adjacent to the user's skin. According to an embodiment, the second communication circuit 102c may establish a direct (e.g., wired) communication channel or a wireless communication channel between the electronic device 101 and the external electronic device 102 or support communication through the established communication channel. According to an embodiment, the second communication circuit 102c may include one or more communication processors supporting direct (e.g., wired) communication or wireless communication. According to an embodiment, the second communication circuit 102c may include a wireless communication circuit (e.g., a cellular communication circuit, a short-range wireless communication circuit, or a global navigation satellite system (GNSS) communication circuit) or a wired communication circuit (e.g., a local area network (LAN) communication circuit or a power line communication (PLC) circuit). A corresponding one of these communication circuits may communicate with the electronic device 101 via the first network (e.g., a short-range communication network, such as Bluetooth™, wireless-fidelity (Wi-Fi) direct, or infrared data association (IrDA)) or the second network (e.g., a long-range communication network, such as a cellular network, the Internet, or a computer network (e.g., LAN or wide area network (WAN)).

Figure 2:
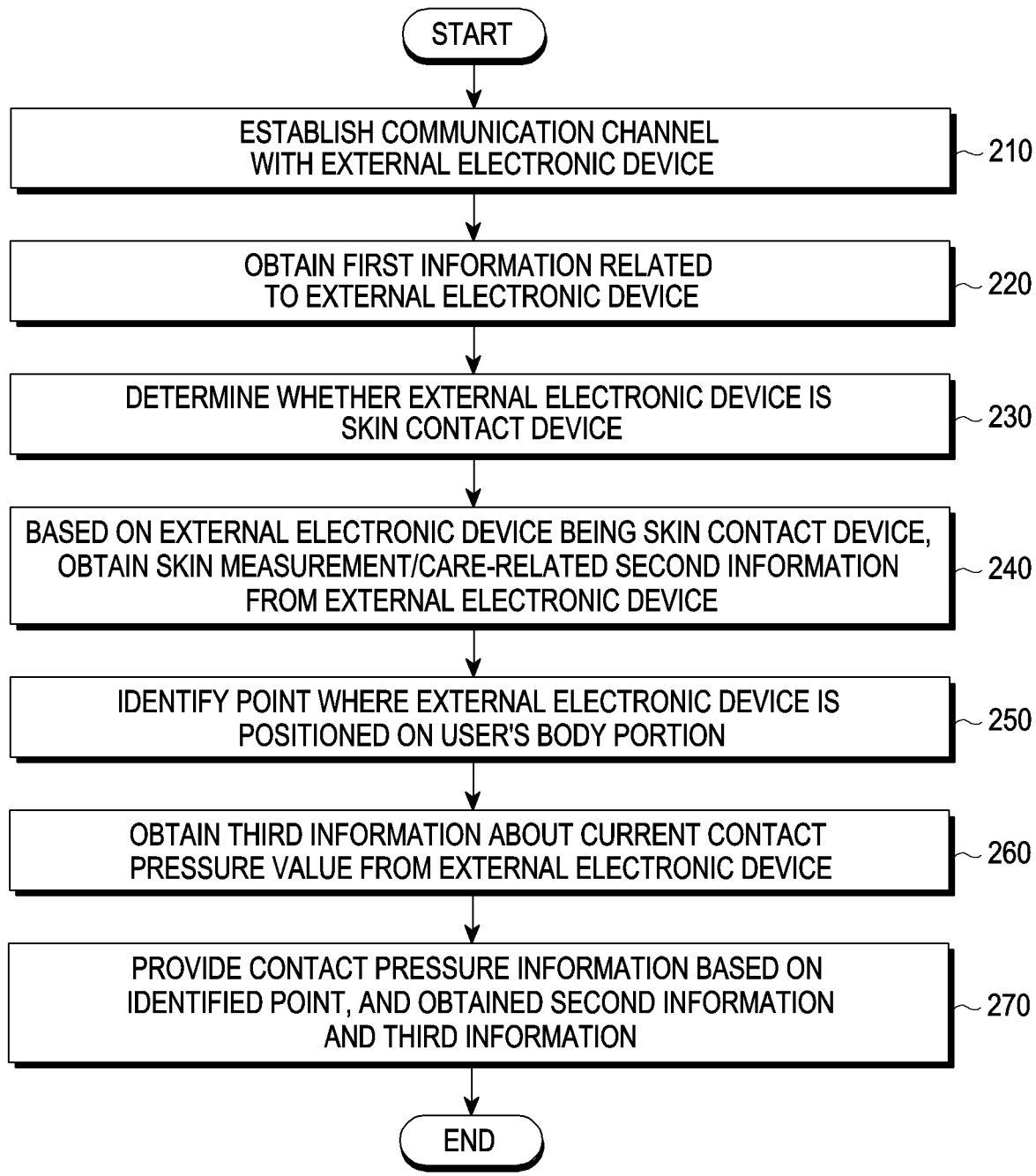
FIG. 2 is a flowchart illustrating an example method for providing contact pressure information by an electronic device according to various embodiments.
Figure 3A:
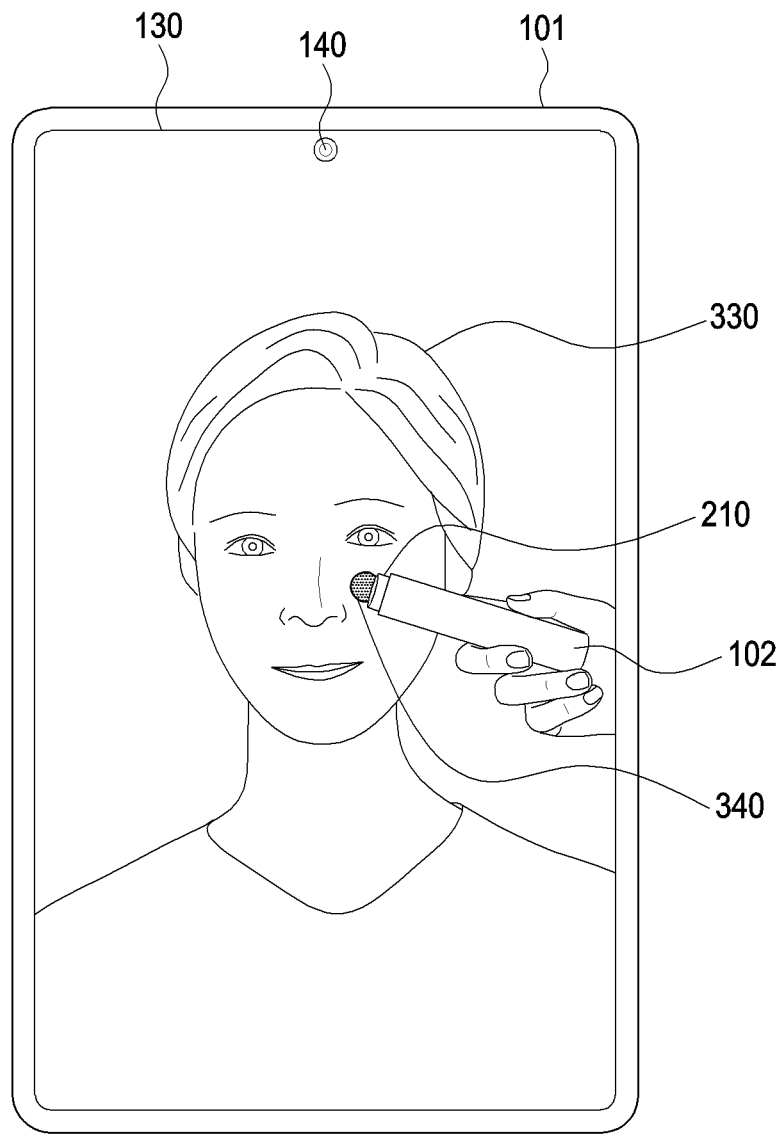
FIGS. 3A and 3B are diagrams illustrating an example method for determining the position of an external electronic device by an electronic device according to various embodiments.
Figure 3B:
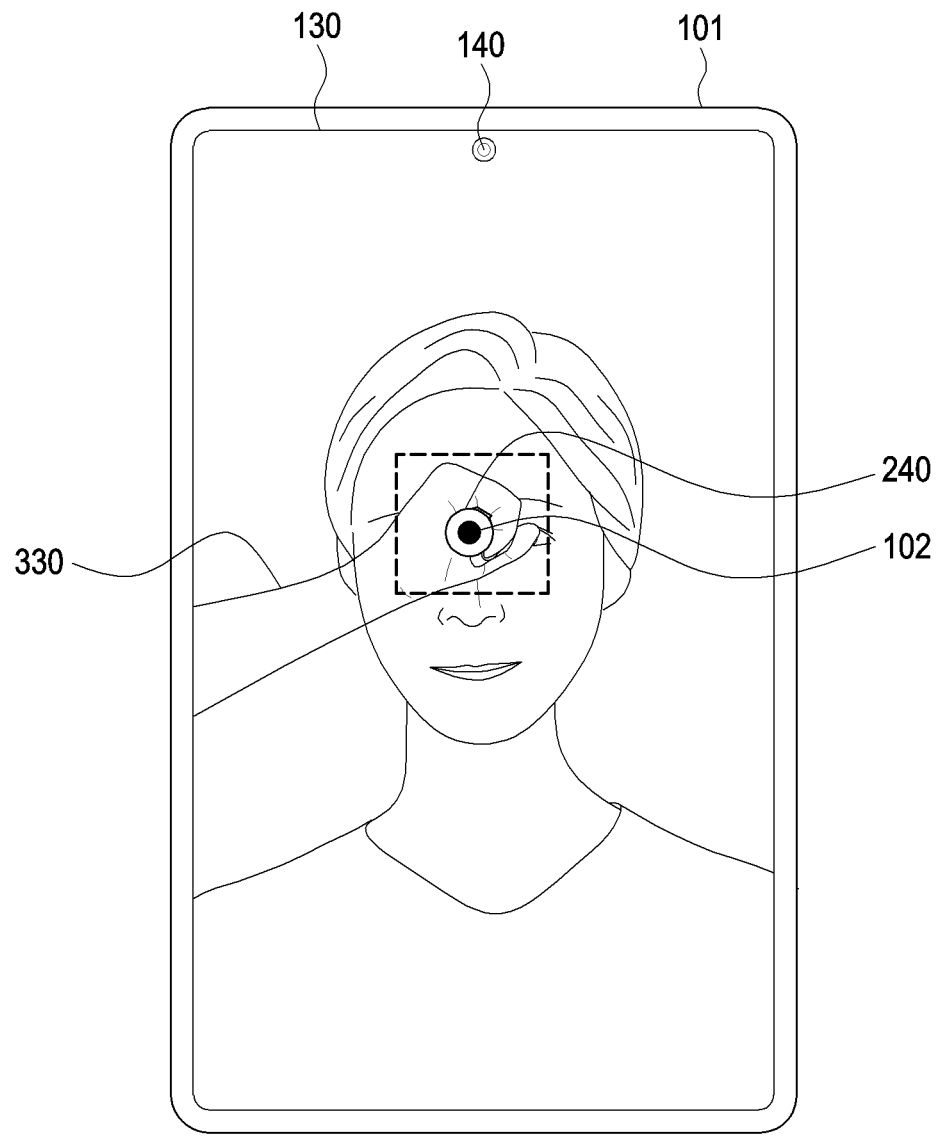

FIG. 2 is a flowchart illustrating an example method for providing contact pressure information by an electronic device according to various embodiments. FIGS. 3A and 3B are diagrams illustrating an example method for determining the position of an external electronic device by an electronic device according to various embodiments. FIGS. 4A, 4B, 4C, and 4D are diagrams illustrating various examples of contact pressure information according to various embodiments.

Referring to FIG. 2, according to an embodiment, the electronic device 101 may establish a communication channel with the external electronic device 102 in operation 210. According to an embodiment, the communication channel may include a wired communication channel or a wireless communication channel. According to an embodiment, the wired communication channel may include, e.g., a local area network (LAN) communication channel or a power line communication channel. According to an embodiment, the wireless communication channel may include, e.g., a short-range communication network communication channel, such as Bluetooth, Wi-Fi direct, or infrared data association (IrDA), or a long-range communication network communication channel, such as cellular network, Internet, or computer network (e.g., LAN or wide area network (WAN)).

According to an embodiment, the electronic device 101 may obtain first information related to the external electronic device 102 in operation 220. According to an embodiment, the first information related to the external electronic device 102 may include at least one of, e.g., information for identifying the type of the external electronic device 102 (e.g., whether the external electronic device 102 is a skin contact device or another type of device), information about the device model name of the external electronic device 102, information about the function supported by the external electronic device 102, information about the shape of the external electronic device 102, or the like.

According to an embodiment, the electronic device 101 may determine whether the external electronic device is a skin contact device in operation 230. According to an embodiment, the electronic device 101 may identify whether the type of the external electronic device 102 is a skin contact device by identifying the first information (e.g., information for identifying the type of the external electronic device 102) obtained from the external electronic device 102.

According to an embodiment, based on the external electronic device 102 being a skin contact device, the electronic device 101 may obtain second information related to skin measurement/care from the external electronic device 102, in operation 240. To that end, according to an embodiment, the electronic device 101 may request the external electronic device 102 to provide skin measurement/care information via the first communication circuit 150. According to an embodiment, the skin measurement/care information may include at least one of information about a recommended measurement position (e.g., a specific point) for performing skin condition measurement or skincare, information about per-part (e.g., the left cheek region, right cheek region, around the chin, and/or the forehead region) proper contact pressure value of the user's body portion (e.g., the face), information about a recommended measurement path for performing skin condition measurement or skincare, or the like. According to an embodiment, the skin measurement/care information may be obtained from a server operably connected with the electronic device 101.

According to an embodiment, the electronic device 101 may identify the point where the external electronic device 102 is positioned on the user's body portion (e.g., the left cheek region) in operation 250. In other words, according to an embodiment, the electronic device 101 may identify what part (e.g., the left cheek region) of the user's body portion (e.g., face) the external electronic device 102 is included. According to an embodiment, as shown in FIG. 3A, the electronic device 101 may identify the shape of a front end 210 of the external electronic device 102 that contacts the user's skin from the identified shape of the external electronic device 102, using the shape of the external electronic device 102 received from the external electronic device 102. According to an embodiment, the processor 110 may identify the shape of the front end of the external electronic device 102 by recognizing the color of the front end 210 of the external electronic device 102 and a designated marker on the front end 210 of the external electronic device 102. According to an embodiment, the processor 110 may identify the point where the shape of the front end 210 of the external electronic device 102 is positioned on the user's skin (e.g., face). According to an embodiment, the processor 110 may identify the point where the external electronic device 102 is positioned on the user's body portion (e.g., face) by identifying the point 340 where the front end shape is positioned on the user's skin (e.g., face). According to an embodiment, there may be such an occasion where the shape of the front end 210 of the external electronic device 102 is not correctly identified by the body of the external electronic device 102 or the user's hand holding the external electronic device 102, as shown in FIG. 3B. For example, as at least part of the shape of the front end 210 of the external electronic device 102 is hidden by the body of the external electronic device 102 or the user's hand holding the external electronic device 102, the shape of the front end 210 of the external electronic device 102 may not correctly be identified, as shown in FIG. 3B. In this case, according to an embodiment, the processor 110 may determine that a substantial center portion 240 of the user's hand or body of the image of the body of the external electronic device 102 or the image of the user's hand obtained by the camera 140 is the point where the front end 210 of the external electronic device 102 is positioned. According to an embodiment, the electronic device 101 may determine what region of the user's body portion the identified position of the front end 210 is included and identify the point where the external electronic device 102 is positioned on the user's body portion. If the identified position of the front end 210 is at a boundary of a specific region, and 80% or more of the area of length (e.g., the horizontal or vertical length or diameter of the captured front end 210) of the front end 210 are included in the specific region, the electronic device 101 may determine that the external electronic device 102 is positioned in the specific region. According to an embodiment, the electronic device 101 may further perform the operation of identifying what part of the user's body portion is displayed on the electronic device 101 before or after performing operation 250. For example, according to an embodiment, the electronic device 101 may detect the user's body portion (e.g., face) using various algorithms for detecting the user's body portion (e.g., face) (e.g., principal component analysis (PCA) using the eigenface, linear discriminate analysis (LDA), elastic bunch graph matching, a hidden Markov model, multilinear subspace learning using a tensor representation or neuronal motivated dynamic link matching) and determine that the detected body portion is the body portion currently displayed on the electronic device 101, thereby identifying what part of the user's body portion is currently displayed on the electronic device 101. According to an embodiment, the electronic device 101 may extract feature points from the user's image displayed on the electronic device 101 and compare the shape formed by the extracted feature points with a template pre-stored in the electronic device 101, thereby identifying what part of the user's body portion is currently displayed on the electronic device 101. According to the above-described operation of detecting the body portion and operation 250, the electronic device 101 may identify what part (e.g., face) of the user's body portion the external electronic device 102 is positioned and may identify what region (e.g., the left cheek region) of the identified part the external electronic device 102 is positioned.

According to an embodiment, in operation 260, the electronic device 101 may obtain third information about the current contact pressure value from the external electronic device 102. According to an embodiment, the processor 110 may request the external electronic device 102 to provide the information about the contact pressure value via the first communication circuit 150. However, the third information, according to an embodiment, may be transmitted to the electronic device 101, along with or included in the second information if the external electronic device 102 contacts the user's skin. In other words, if a contact of the external electronic device 102 to the user's skin is detected, the information about the current contact pressure value, according to an embodiment, may be transmitted from the external electronic device 102 to the electronic device 101 even before operation 250 is performed. According to an embodiment, the information about the contact pressure value may be transmitted to the electronic device 101 automatically without receiving a request from the electronic device 101 if a contact of the external electronic device 102 to the user's skin is detected.

Figure 4A:
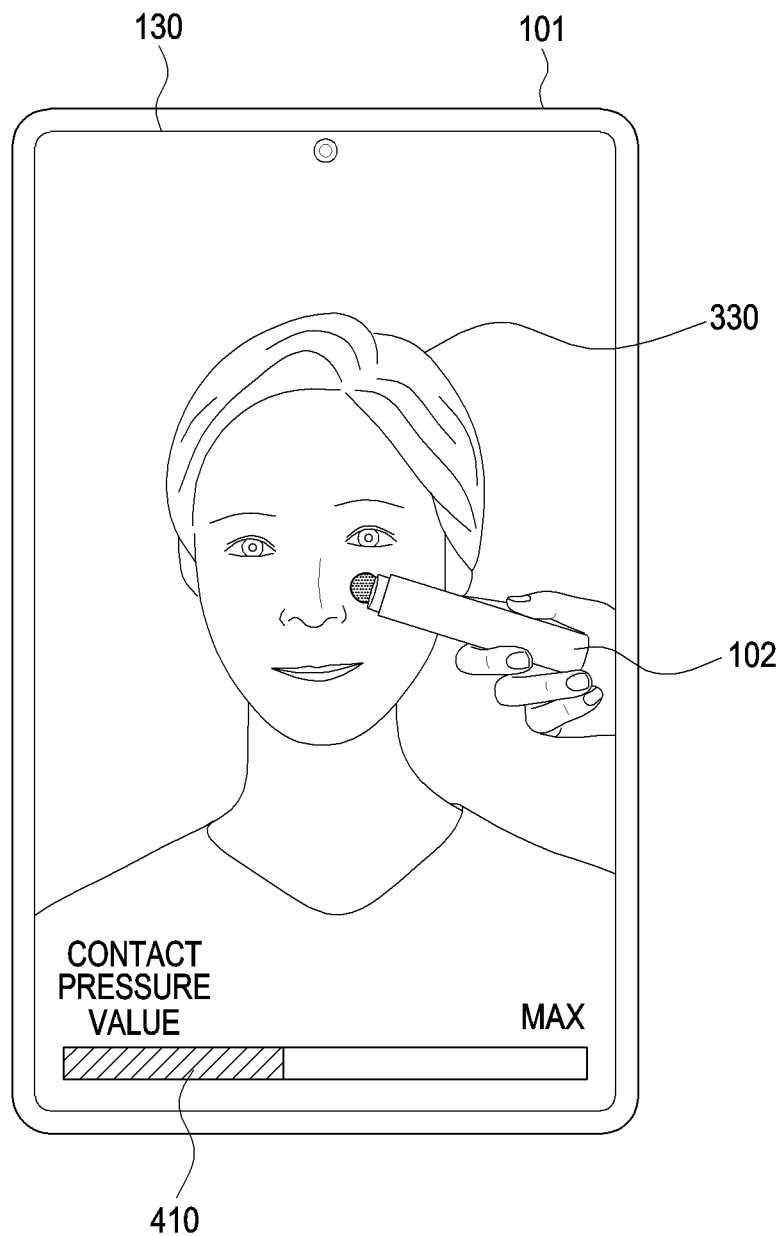
FIGS. 4A, 4B, 4C, and 4D are diagrams illustrating various examples of contact pressure information according to various embodiments.
Figure 4B:
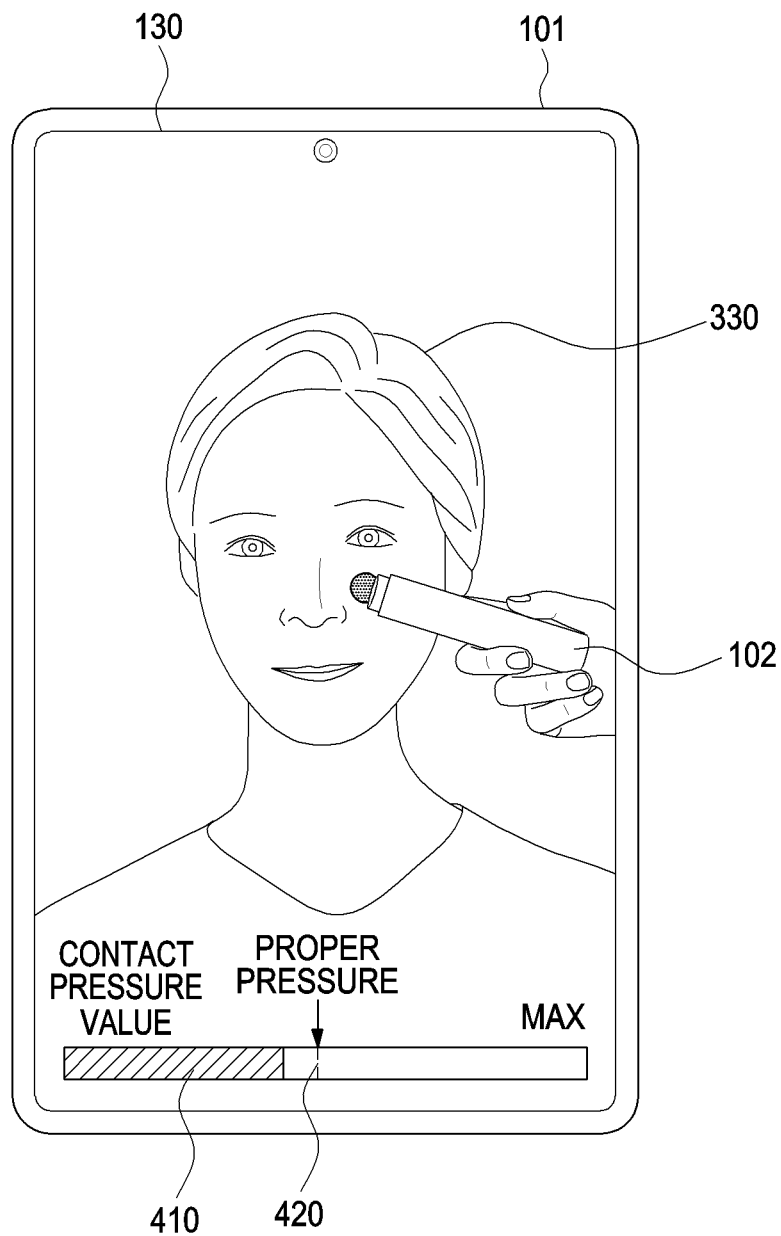
Figure 4C:
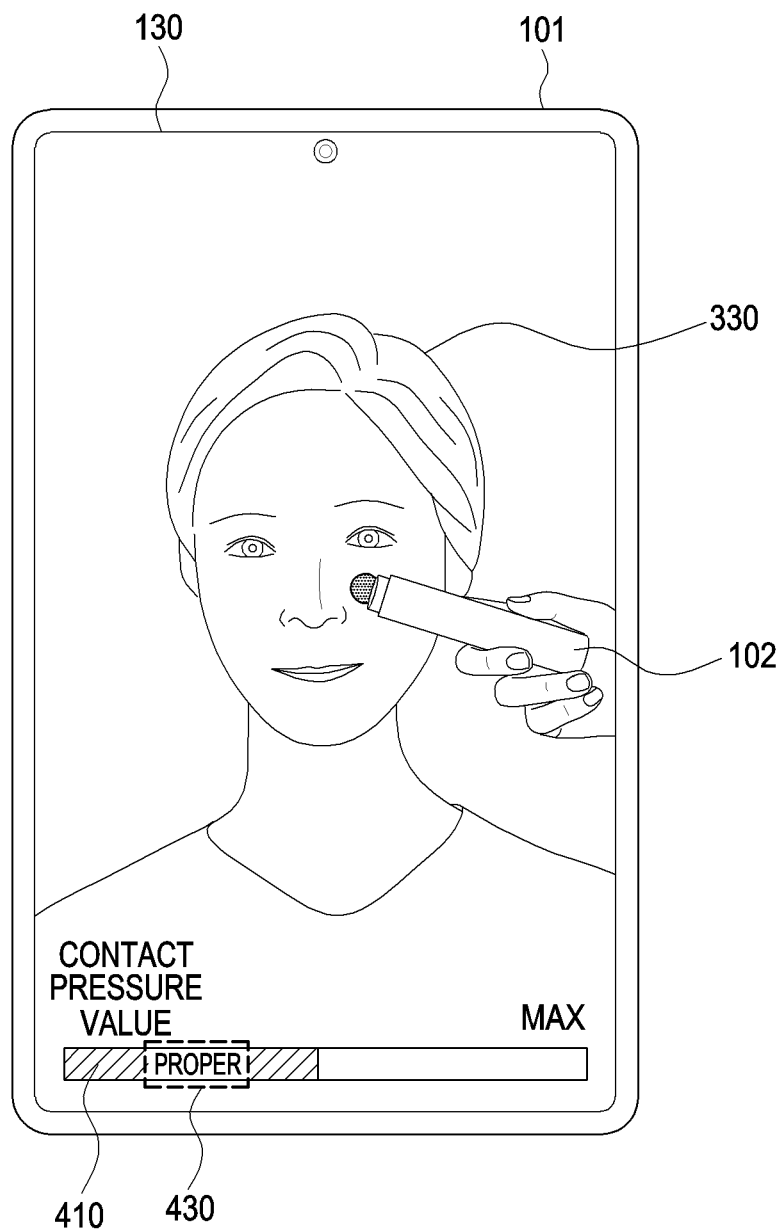

According to an embodiment, in operation 270, the electronic device 101 may provide contact pressure information using the identified point (e.g., the left cheek), the obtained second information (e.g., a proper contact pressure value for the left cheek region), and third information (e.g., the current contact pressure value). For example, according to an embodiment, the electronic device 101 may output the information 410 (e.g., the relative value or absolute value) about the current contact pressure value via the display 130 as shown in FIG. 4A. According to an embodiment, the electronic device 101 may set the information about the per-part proper pressure value of the user's body portion (e.g., face) received from the external electronic device 102, as a recommended contact pressure value and output the information 410 about the current contact pressure value and the information 420 about the recommended contact pressure value via the display 130, as shown in FIG. 4B. According to an embodiment, the electronic device 101 may compare the information about the per-part (e.g., the left cheek, right cheek, around the chin, and/or the forehead) proper contact pressure value of the user's body portion (e.g., face) received from the external electronic device 102 with the obtained contact pressure value, determine whether the current contact pressure value is a proper contact pressure, and output information (e.g., proper) 430 about the result of the determination via the display 130, as shown in FIG. 4C. In this case, according to an embodiment, the electronic device 101 may display the current contact pressure value 410 along with the information (e.g., proper) 430 about the result of determination. Alternatively, the electronic device 101 may display only the information (e.g., proper) 430 about the result of determination. According to an embodiment, the electronic device 101 may output the current contact pressure value measured and contact pressure values for the contacts made during a specific period (e.g., one week) via the display 130. According to an embodiment, the processor 110 may compute the average contact pressure value for the contacts made to a specific point (e.g., the right cheek) during a specific period (e.g., one week), stored in the memory 120. According to an embodiment, the processor 110 may compare the computed average contact pressure value with the current contact pressure value received from the external electronic device 102. Thus, skin condition measurement or skincare may be performed constantly under the same or similar pressure condition, delivering a reliable result of skin condition measurement or skincare.

Figure 5A:
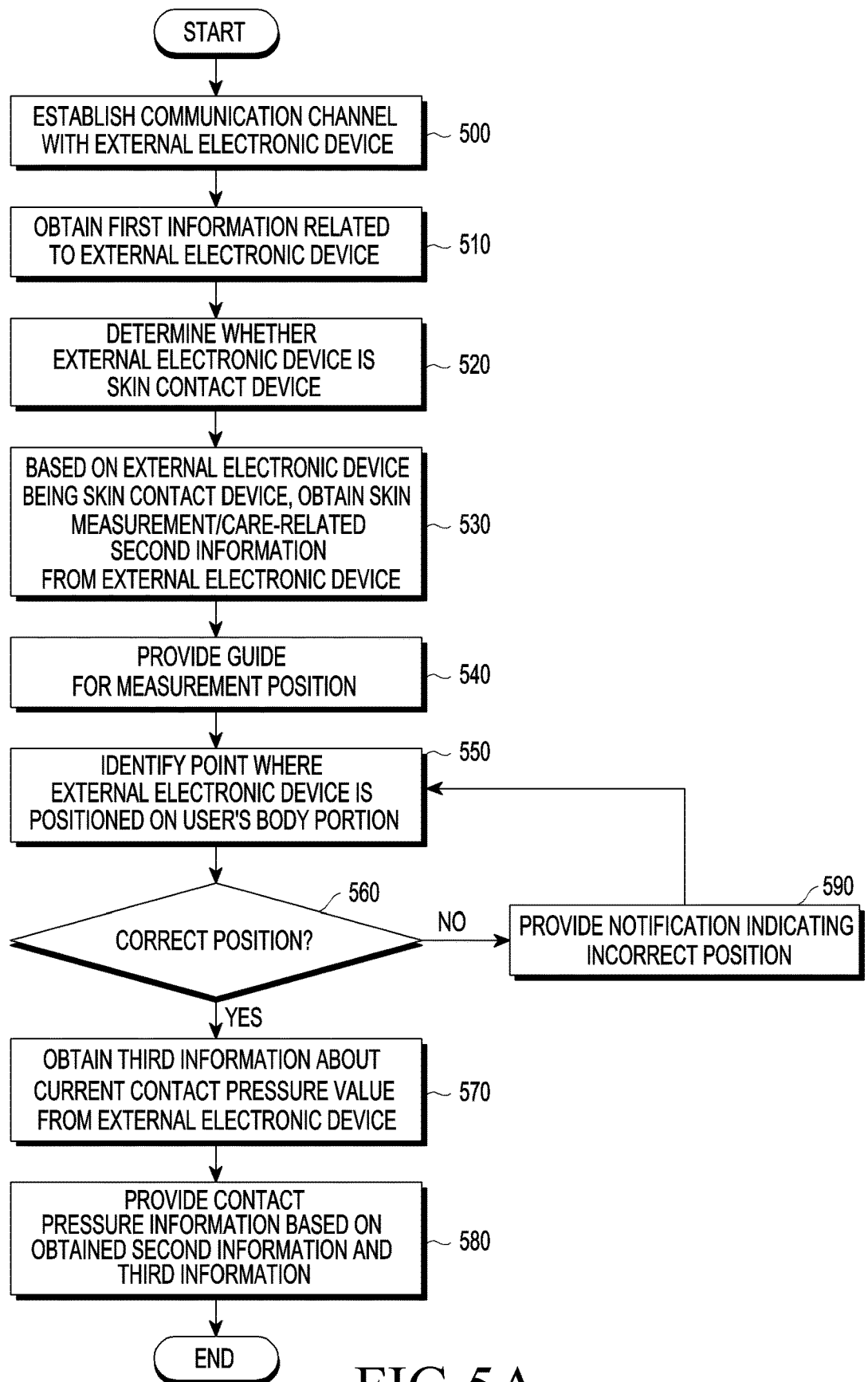
FIG. 5A is a flowchart illustrating an example method for providing a guide for a pre-measured measurement position and providing contact pressure information, by an electronic device, according to various embodiments.
Figure 5B:
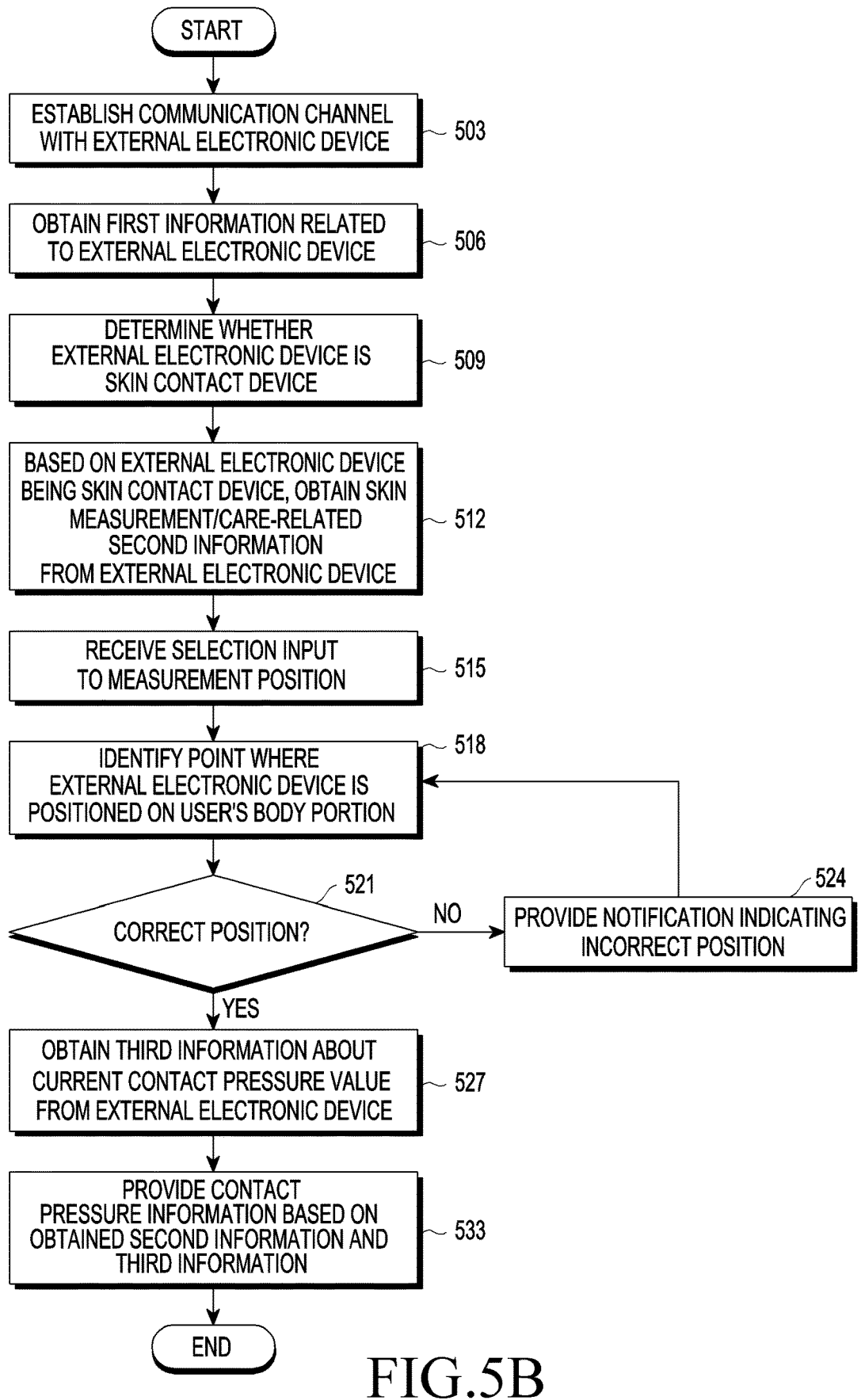
FIG. 5B is a flowchart illustrating an example method for providing contact pressure information after determining a measurement position according to a selection input by an electronic device, according to various embodiments.

FIGS. 5A and 5B are flowcharts illustrating an example method for providing a guide for a pre-measured measurement position and then providing contact pressure information, by an electronic device, according to various embodiments. FIGS. 6A, 6B, 6C, and 6D are diagrams illustrating an example of the method of FIGS. 5A and 5B according to various embodiments.

Referring to FIG. 5A, according to an embodiment, the electronic device 101 may establish a communication channel with the external electronic device 102 in operation 500. According to an embodiment, the communication channel may include a wired communication channel or a wireless communication channel. According to an embodiment, the wired communication channel may include, e.g., a local area network (LAN) communication channel or a power line communication channel. According to an embodiment, the wireless communication channel may include, e.g., a short-range communication network communication channel, such as Bluetooth, Wi-Fi direct, or infrared data association (IrDA), or a long-range communication network communication channel, such as cellular network, Internet, or computer network (e.g., LAN or wide area network (WAN)).

According to an embodiment, the electronic device 101 may obtain first information related to the external electronic device in operation 510. According to an embodiment, the first information related to the external electronic device 102 may include at least one of, e.g., information for identifying the type of the external electronic device 102 (e.g., whether the external electronic device 102 is a skin contact device or another type of device), information about the device model name of the external electronic device 102, information about the function supported by the external electronic device 102, or information about the shape of the external electronic device 102.

According to an embodiment, the electronic device 101 may determine whether the external electronic device 102 is a skin contact device in operation 520. According to an embodiment, the electronic device 101 may identify whether the type of the external electronic device 102 is a skin contact device by identifying the first information (e.g., information for identifying the type of the external electronic device 102) obtained from the external electronic device 102.

According to an embodiment, when the external electronic device 102 is a skin contact device, the electronic device 101 may obtain second information related to skin measurement/care from the external electronic device 102, in operation 530. According to an embodiment, the second information related to skin measurement/care may include at least one of information about a recommended measurement position (e.g., a specific point) for performing skin condition measurement or skincare, information about per-part (e.g., the left cheek, right cheek, around the chin, and/or the forehead) proper contact pressure value of the user's body portion (e.g., the face), or information about a recommended measurement path for performing skin condition measurement or skincare.

Figure 6A:
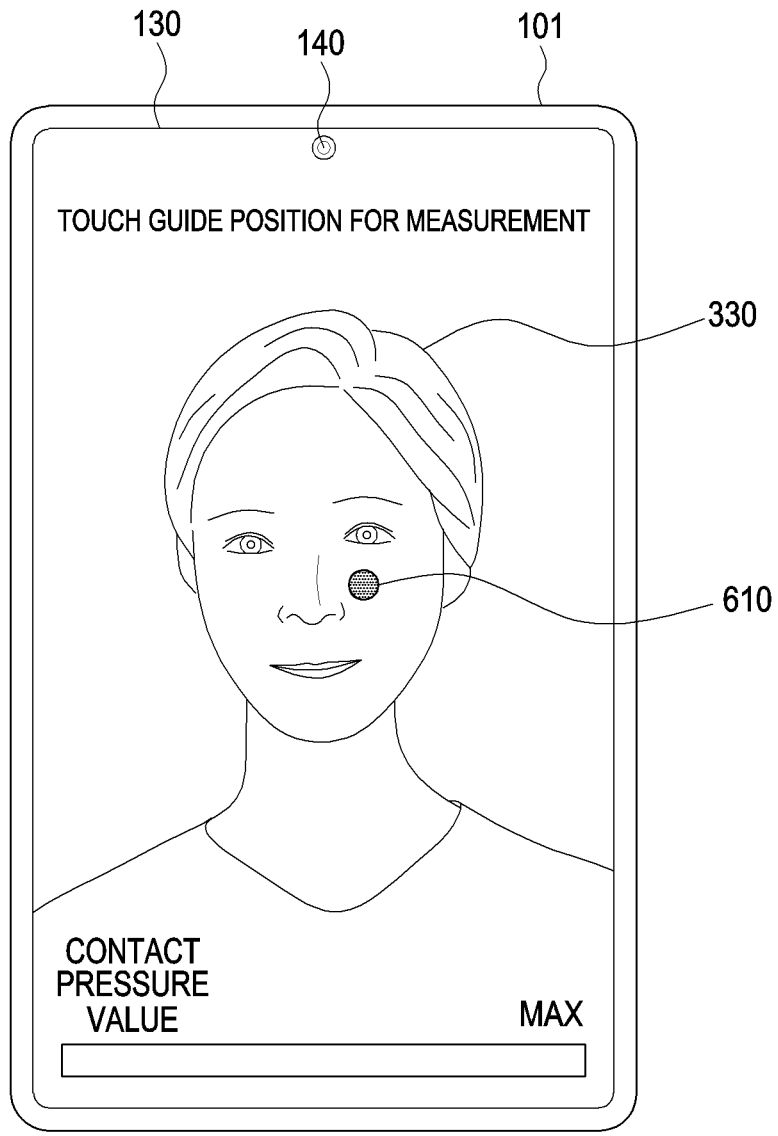
FIGS. 6A, 6B, 6C, and 6D are diagrams illustrating an example of the method of FIGS. 5A and 5B according to various embodiments.

According to an embodiment, the electronic device 101 may provide a guide for measurement position in operation 540. According to an embodiment, the electronic device 101 may provide a guide for measurement position using the obtained second information (e.g., information about a recommended measurement position (e.g., a specific point) for performing skin condition measurement or skincare). According to an embodiment, the guide 610 (refer to FIG. 6A) for measurement position may be displayed in an augmented reality (AR) manner on the screen where the body portion (e.g., face) of the user 330 is displayed as shown in FIG. 6A but is not limited thereto. To provide the guide 610 for measurement position, according to an embodiment, the electronic device 101 may identify feature points (in other words, a land mark) of the body portion of the user 330. According to an embodiment, the electronic device 101 may identify the body portion of the user 330 to thereby identify the shape of the body portion and display the guide 610 for measurement position in the position indicated by a recommended measurement position included in the second information, based on the identified shape of the body portion.

According to an embodiment, the electronic device 101 may identify the point where the external electronic device 102 is positioned on the user's body portion in operation 550. The description made above in connection with operation 250 may apply to the following description.

Figure 6B:
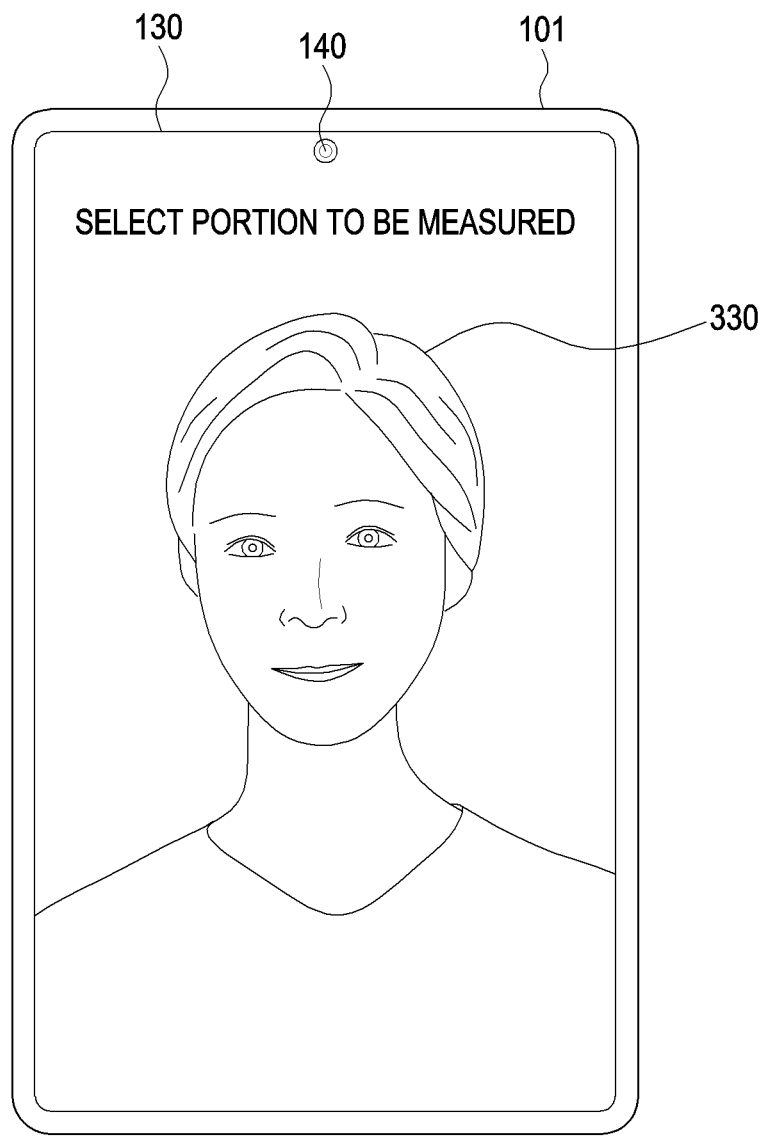
Figure 6C:
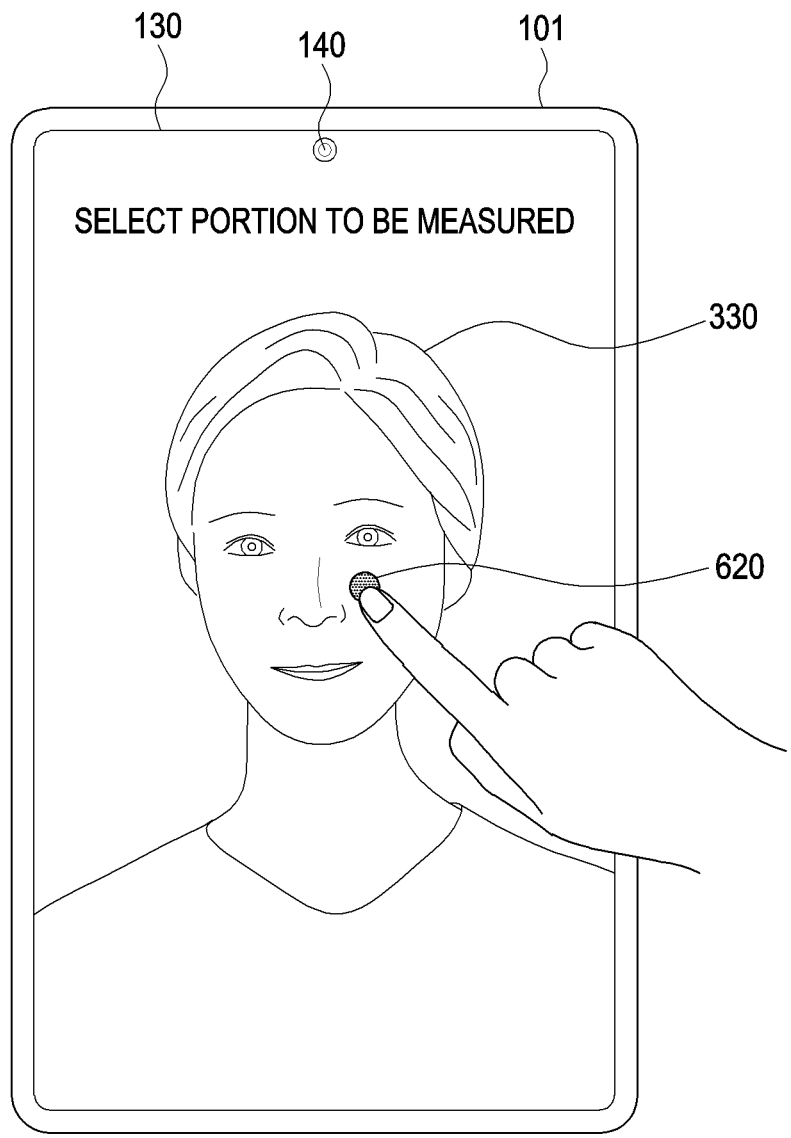
Figure 6D:
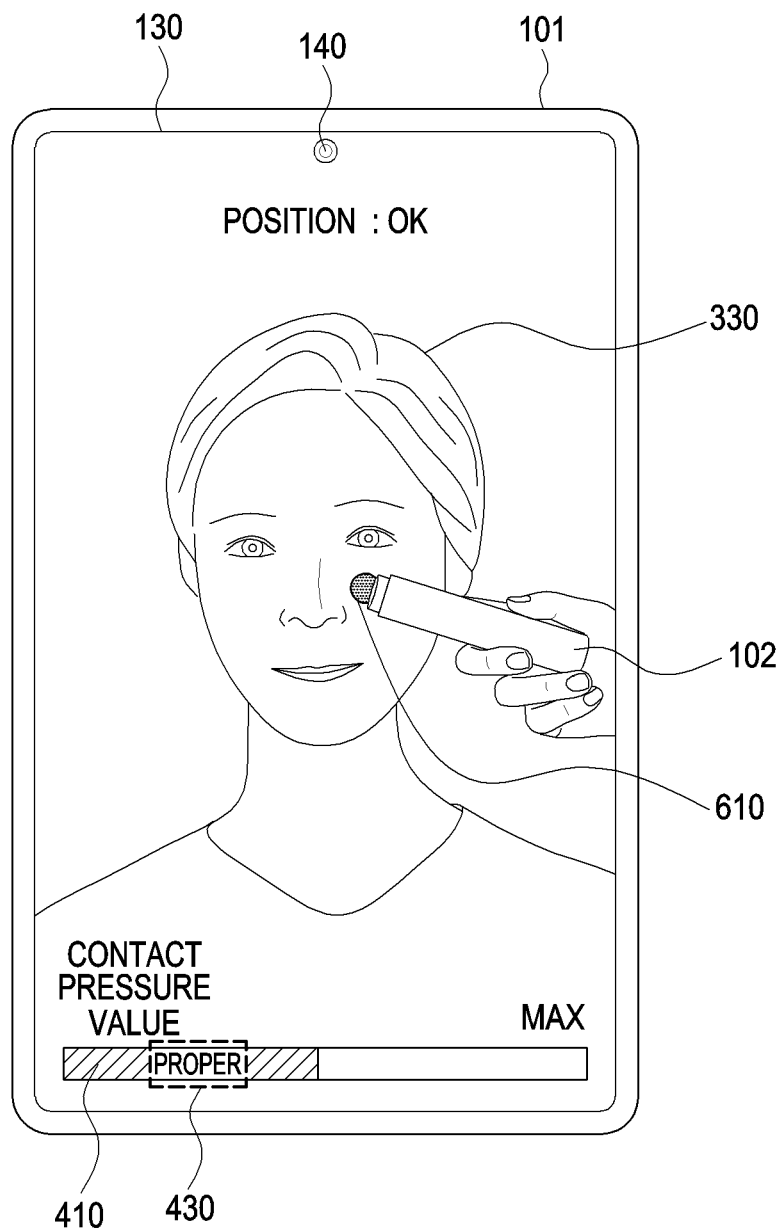

According to an embodiment, in operation 560, the electronic device 101 may determine whether the external electronic device 102 is positioned at a correct point. According to an embodiment, the electronic device 101 may determine whether the position of the external electronic device 102 identified by operation 560 matches the position indicated by the guide 610 for measurement position. For example, according to an embodiment, the electronic device 101 may determine that the external electronic device 102 is positioned at the correct point when 80% or more of the area or length (e.g., the horizontal or vertical length, or the diameter of the captured front end 210) of the front end 210 of the external electronic device 102 are included in the area of the guide 610 for measurement position. According to an embodiment, when the external electronic device 102 is positioned at the correct point, the electronic device 101 may display a notification message (e.g., "Position: OK") as shown in FIG. 6D.

According to an embodiment, in operation 570, the electronic device 101 may obtain third information about the current contact pressure value from the external electronic device 102. According to an embodiment, the electronic device 101 may request the external electronic device 102 to provide the information about the contact pressure value via the first communication circuit 150. However, the third information, according to an embodiment, may be transmitted to the electronic device 101, along with or included in the second information if the external electronic device 102 contacts the user's skin. In other words, if a contact of the external electronic device 102 to the user's skin is detected, the information about the current contact pressure value, according to an embodiment, may be transmitted from the external electronic device 102 to the electronic device 101 even before operations 550 and 560 are performed. According to an embodiment, the information about the contact pressure value may be transmitted to the electronic device 101 automatically without receiving a request from the electronic device 101 if a contact of the external electronic device 102 to the user's skin is detected.

According to an embodiment, the electronic device 101 may provide contact pressure information based on the obtained second information and third information in operation 580. For example, according to an embodiment, the electronic device 101 may output the information 410 (e.g., the relative value or absolute value) about the current contact pressure value via the display 130 as shown in FIG. 4A. According to an embodiment, the electronic device 101 may set the information about the per-part proper pressure value of the user's body portion (e.g., face) received from the external electronic device 102, as a recommended contact pressure value and output the information 410 about the current contact pressure value and the information 420 about the recommended contact pressure value via the display 130, as shown in FIG. 4B. According to an embodiment, the electronic device 101 may compare the information about the per-part (e.g., the left cheek, right cheek, around the chin, and/or the forehead) proper contact pressure value of the user's body portion (e.g., face) received from the external electronic device 102 with the obtained contact pressure value, determine whether the current contact pressure value is a proper contact pressure, and output information (e.g., proper) 430 about the result of the determination via the display 130, as shown in FIG. 4C or 6D. In this case, according to an embodiment, the electronic device 101 may display the current contact pressure value 410 along with the information (e.g., proper) 430 about the result of determination. The electronic device 101 may display only the information (e.g., proper) 430 about the result of determination. According to an embodiment, the electronic device 101 may output the current contact pressure value measured and contact pressure values for the contacts made during a specific period (e.g., one week) via the display 130. To that end, according to an embodiment, the processor 110 may compute the average contact pressure value for the contacts made to a specific point (e.g., the right cheek) during a specific period (e.g., one week), stored in the memory 120. According to an embodiment, the processor 110 may compare the computed average contact pressure value with the current contact pressure value received from the external electronic device 102. Thus, skin condition measurement or skincare may be performed constantly under the same or similar pressure condition, delivering a reliable result of skin condition measurement or skincare.

According to an embodiment, the electronic device 101 may provide a notification indicating that the external electronic device 102 is not positioned at the correct point when the external electronic device 102 is positioned at an incorrect point (e.g., 80% or more of the area or length (e.g., the horizontal or vertical length, or the diameter of the captured front end 210) of the front end 210 of the external electronic device 102 are not included in the area of the guide 610 for measurement position in operation 590. According to an embodiment, the notification may include at least one of a visual notification (e.g., displaying a message), an auditory notification (e.g., outputting a sound message), or a tactile notification (e.g., a vibration).

FIG. 5B is a flowchart illustrating an example method for providing contact pressure information after determining a measurement position according to a user's selection input by an electronic device, according to various embodiments. FIGS. 6A, 6B, 6C, and 6D are diagrams illustrating an example of the method of FIGS. 5A and 5B. The description of operations 500 to 530 of FIG. 5A may be applied to operations 503 to 512 of FIG. 5B.

Referring to FIG. 5B, according to an embodiment, the electronic device 101 may receive a selection input for measurement position in operation 515. Referring to FIG. 6B, according to an embodiment, the electronic device 101 may display a captured image of the user 330 on the display 130. According to an embodiment, the electronic device 101 may receive a user input (e.g., a touch input) 620 for selecting a measurement part as shown in FIG. 6C. According to an embodiment, upon receiving a user input (e.g., a touch input) for selecting a measurement part, the electronic device 101 may determine that the selected measurement part is a point for performing skin condition measurement or skincare. The description of operations 550 to 590 of FIG. 5A may be applied to operations 518 to 533.

Figure 7A:
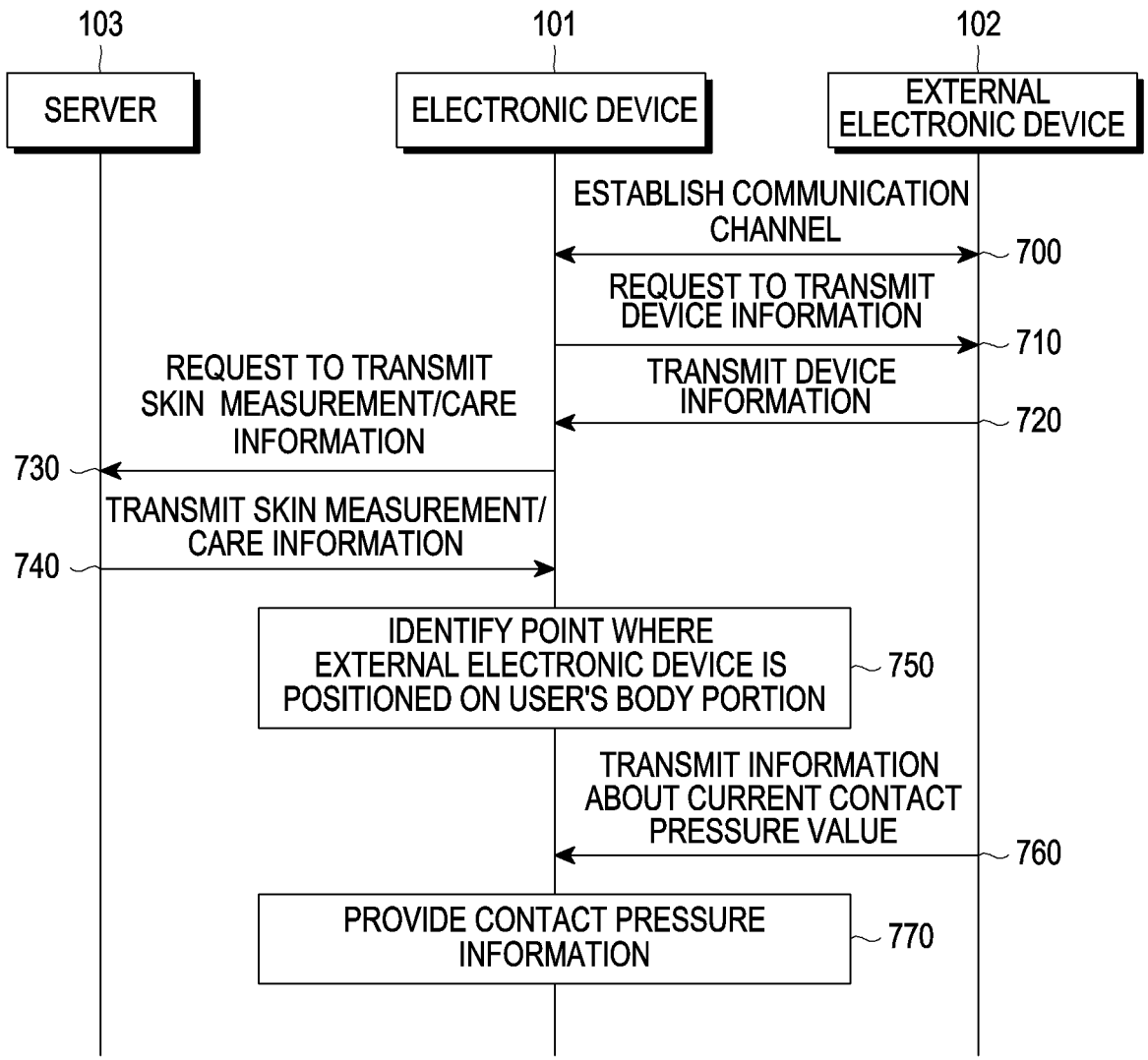
FIGS. 7A, 7B, and 7C are signal flow diagrams illustrating an example of receiving first information related to an external electronic device from a server, in the various embodiments described above in connection with FIGS. 1A, 1B, 1C, 1D, 2, 3A, 3B, 4A, 4B, 4C, 4D, 5A, 5B, 6A, 6B, 6C and 6D according to various embodiments.
Figure 7B:
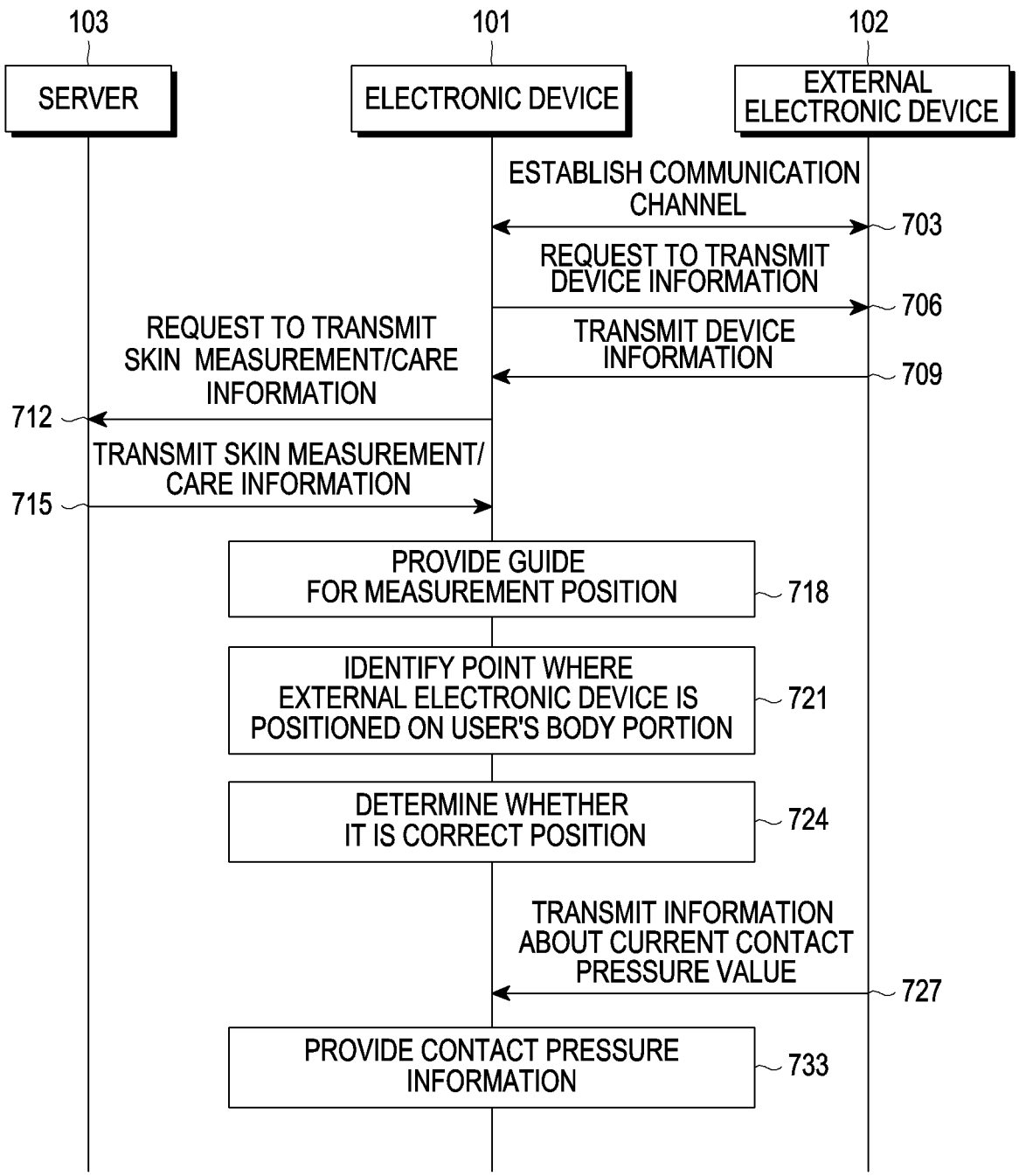
Figure 7C:
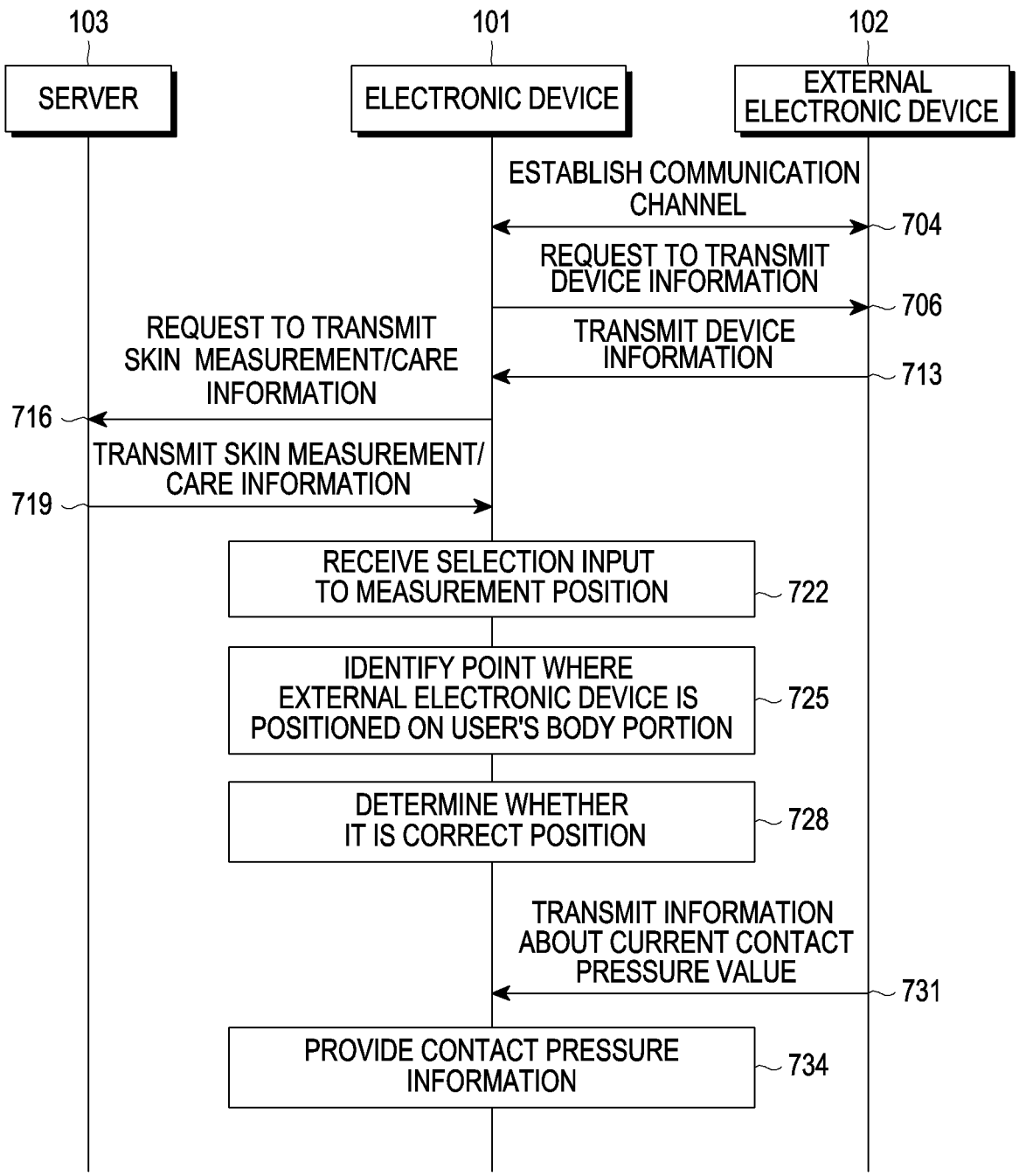

FIGS. 7A, 7B and 7C are signal flow diagrams illustrating examples of receiving information related to skin measurement/care from a server 103, described above in connection with FIGS. 1A, 1B, 1C, 1D, 3A, 3B, 4A, 4B, 4C, 4D, 5A, 5B, 6A, 6B, 6C and 6D according to various embodiments.

Referring to FIG. 7A, according to an embodiment, the electronic device 101 and the external electronic device 102 may establish a communication channel in operation 700. According to an embodiment, the communication channel may include a wired communication channel or a wireless communication channel. According to an embodiment, the wired communication channel may include, e.g., a local area network (LAN) communication channel or a power line communication channel. According to an embodiment, the wireless communication channel may include, e.g., a short-range communication network communication channel, such as Bluetooth, Wi-Fi direct, or infrared data association (IrDA), or a long-range communication network communication channel, such as cellular network, Internet, or computer network (e.g., LAN or wide area network (WAN)).

According to an embodiment, the electronic device 101 may request the external electronic device 102 to transmit device information of the external electronic device 102 in operation 710. According to an embodiment, the external electronic device 102 may transmit device information to the electronic device 101 according to the request from the electronic device 101 in operation 720. According to an embodiment, the device information about the external electronic device 102 may include at least one of, e.g., information for identifying the type of the external electronic device 102 (e.g., whether the external electronic device 102 is a skin contact device or another type of device), information about the device model name of the external electronic device 102, information about the function supported by the external electronic device 102, or information about the shape of the external electronic device 102.

According to an embodiment, in operation 730, the electronic device 101 may request the server 103 to transmit skin measurement/care information. According to an embodiment, the server 103 may transmit skin measurement/care information to the electronic device 101 according to the request from the electronic device 101 in operation 740. According to an embodiment, the skin measurement/care information may include at least one of information about a recommended measurement position (e.g., a specific point) for performing skin condition measurement or skincare, information about per-part (e.g., the left cheek, right cheek, around the chin, and/or the forehead) proper contact pressure value of the user's body portion (e.g., the face), or information about a recommended measurement path for performing skin condition measurement or skincare. The description of operations 250, 260 and 270 may be applied to operations 750, 760 and 770. What has been described above in connection with FIGS. 5A and 5B may be applied to the other operations of FIGS. 7B and 7C than the operation of requesting the server 103 to transmit skin measurement/care information (operation 712 of FIG. 7B and operation 716 of FIG. 7C) and the operation of receiving skin measurement/care information from the server 103 at the request (operation 715 of FIG. 7B and operation 719 of FIG. 7C), and detailed description thereof may not be repeated here.

Figure 8:
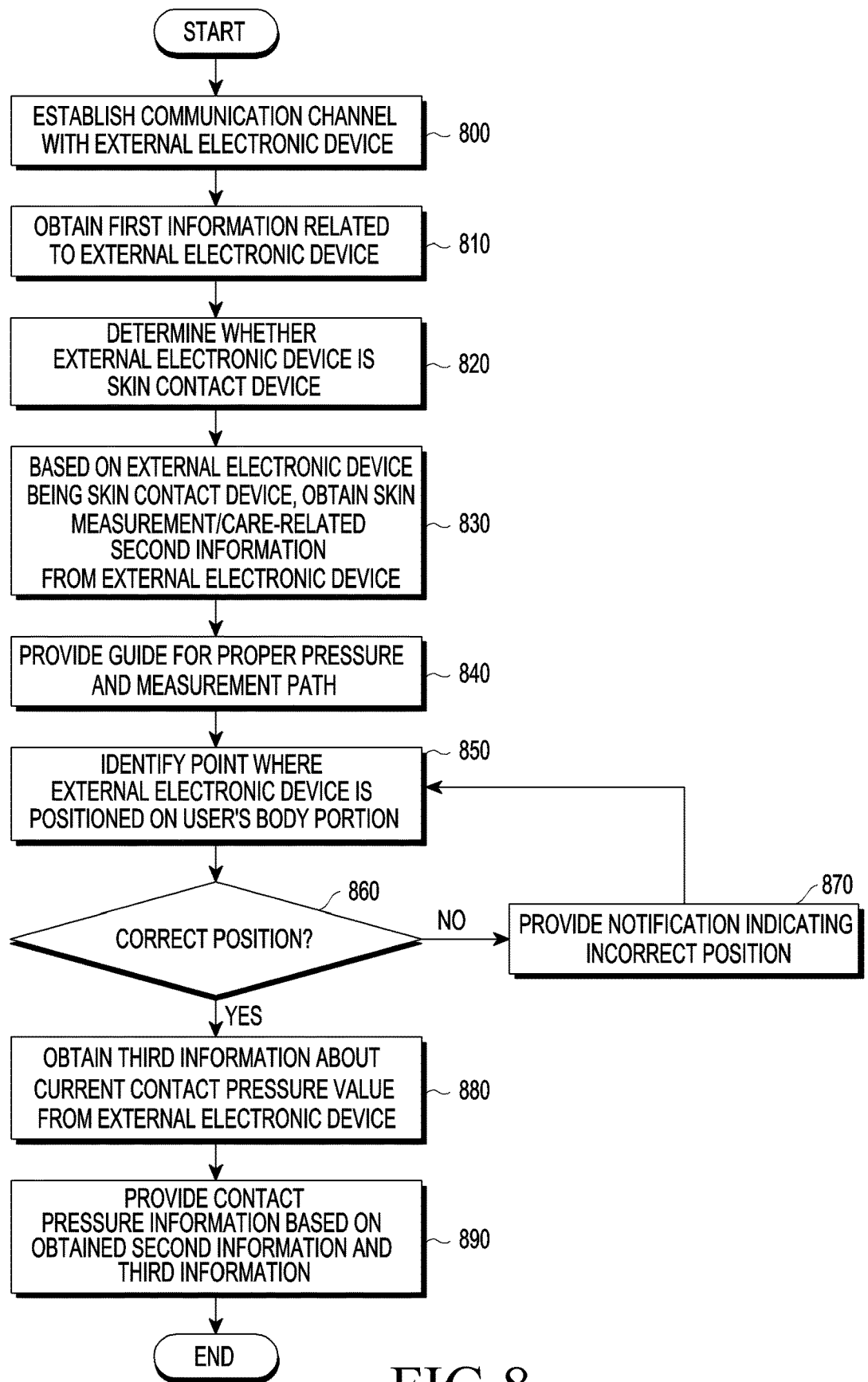
FIG. 8 is a flowchart illustrating an example method for providing contact pressure information after providing a guide for a proper pressure and measurement path according to various embodiments.
Figure 9A:
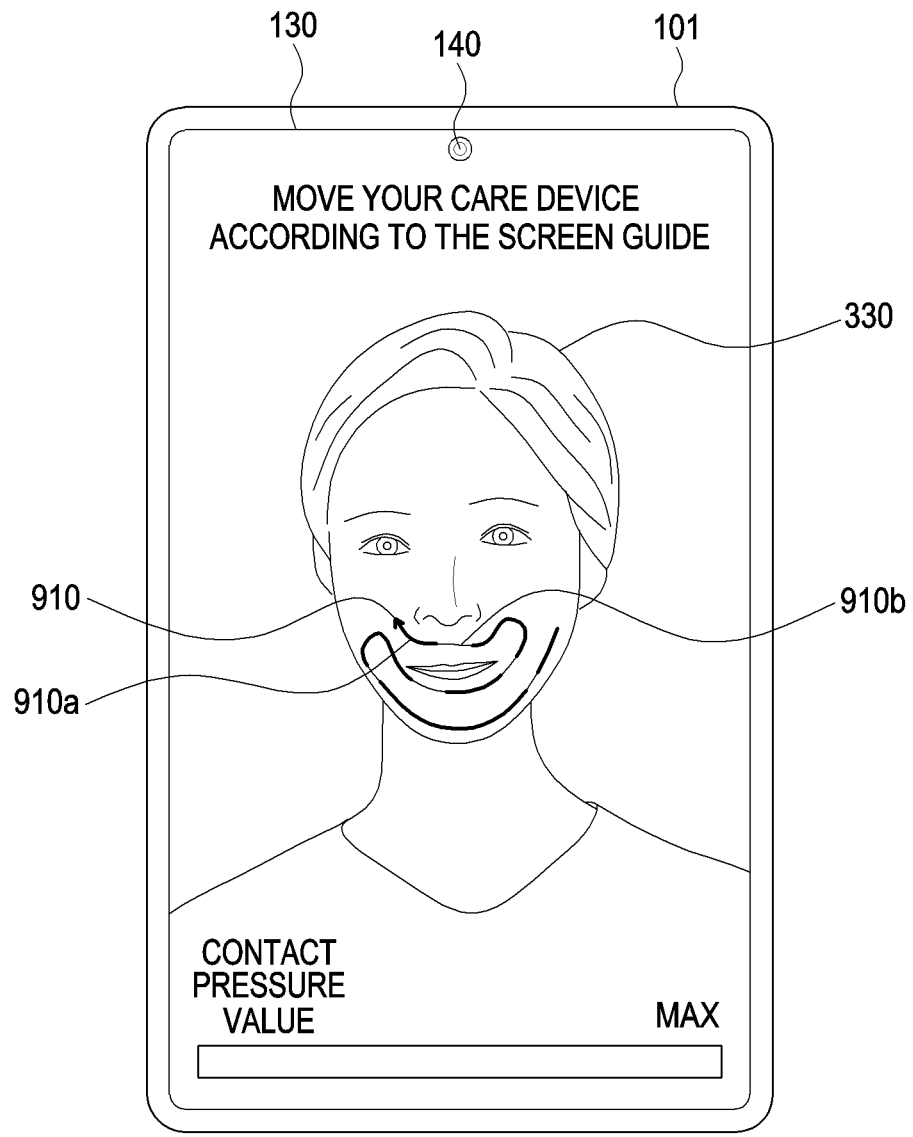
FIGS. 9A and 9B are diagrams illustrating an example of the method of FIG. 8 according to various embodiments.
Figure 9B:
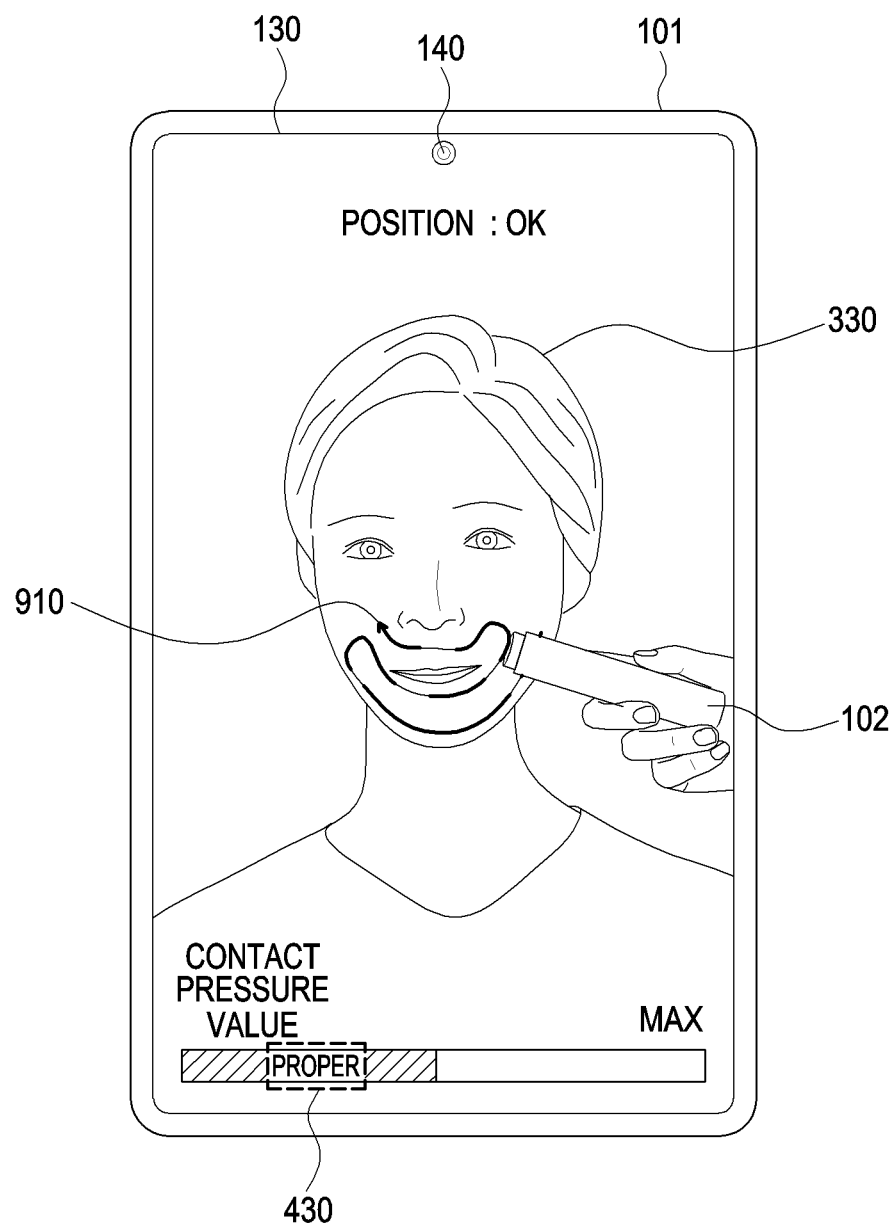

FIG. 8 is a flowchart illustrating an example method for providing contact pressure information after providing a guide for a proper pressure and measurement path according to various embodiments. FIGS. 9A and 9B are diagrams illustrating an example of the method of FIG. 8 according to various embodiments.

Referring to FIG. 8, according to an embodiment, the electronic device 101 may establish a communication channel with the external electronic device 102 in operation 800. According to an embodiment, the communication channel may include a wired communication channel or a wireless communication channel. According to an embodiment, the wired communication channel may include, e.g., a local area network (LAN) communication channel or a power line communication channel. According to an embodiment, the wireless communication channel may include, e.g., a short-range communication network communication channel, such as Bluetooth, Wi-Fi direct, or infrared data association (IrDA), or a long-range communication network communication channel, such as cellular network, Internet, or computer network (e.g., LAN or wide area network (WAN)).

According to an embodiment, the electronic device 101 may obtain first information related to the external electronic device in operation 810. According to an embodiment, the first information related to the external electronic device 102 may include at least one of, e.g., information for identifying the type of the external electronic device 102 (e.g., whether the external electronic device 102 is a skin contact device or another type of device), information about the device model name of the external electronic device 102, information about the function supported by the external electronic device 102, or information about the shape of the external electronic device 102.

According to an embodiment, the electronic device 101 may determine whether the external electronic device 102 is a skin contact device in operation 820. According to an embodiment, the electronic device 101 may identify whether the type of the external electronic device 102 is a skin contact device by identifying the first information (e.g., information for identifying the type of the external electronic device 102) obtained from the external electronic device 102.

According to an embodiment, when the external electronic device 102 is a skin contact device, the electronic device 101 may obtain second information related to skin measurement/care from the external electronic device 102, in operation 830. According to an embodiment, the second information related to skin measurement/care may include at least one of information about a recommended measurement position (e.g., a specific point) for performing skin condition measurement or skincare, information about per-part (e.g., the left cheek, right cheek, around the chin, and/or the forehead) proper contact pressure value of the user's body portion (e.g., the face), or information about a recommended measurement path for performing skin condition measurement or skincare.

According to an embodiment, the electronic device 101 may provide a guide 910 (refer to FIGS. 9A and 9B) for a proper pressure and measurement path in operation 840. According to an embodiment, the electronic device 101 may provide the guide 910 for the proper pressure and measurement path using the obtained second information (e.g., information about a recommended measurement path for performing skin condition measurement or skincare). According to an embodiment, the guide 910 for the proper pressure and measurement path may be displayed in an augmented reality (AR) manner on the screen where the body portion (e.g., face) of the user 330 is displayed as shown in FIG. 9A but is not limited thereto. To provide the guide 910 for the proper pressure and measurement path, according to an embodiment, the electronic device 101 may identify feature points (in other words, a land mark) of the body portion of the user 330. According to an embodiment, the electronic device 101 may identify the body portion of the user 330 to thereby identify the shape of the body portion and display the guide 910 for the proper pressure and measurement path in the position indicated by a recommended measurement position included in the second information, based on the identified shape of the body portion. According to an embodiment, the electronic device 101 may indirectly indicate a proper pressure for a specific portion by displaying the guide 910 for the proper pressure and measurement path in a different thickness. For example, when the thickness of the guide 910 for the proper pressure and measurement path is relatively large (e.g., a thick path 910*a*), the user may be indirectly informed that this portion requires a relatively higher contact pressure. When the thickness of the guide 910 for the proper pressure and measurement path is relatively small (e.g., a thin path 910*b*), the user may be indirectly informed that this portion requires a relatively lower contact pressure.

According to an embodiment, the electronic device 101 may identify the point where the external electronic device 102 is positioned on the user's body portion in operation 850. The description made above in connection with operation 250 may apply to the following description.

According to an embodiment, in operation 860, the electronic device 101 may determine whether the external electronic device 102 is positioned at a correct point. According to an embodiment, the electronic device 101 may determine whether the position of the external electronic device 102 identified by operation 850 matches the position indicated by the guide 910 for the proper pressure and measurement path. For example, according to an embodiment, when the region of the captured front end 210 covers the measurement path or at least part of the edge (or diameter) of the captured front end 210 abuts the measurement path, the electronic device 101 may determine that the identified position of the external electronic device 102 matches the position indicated by the guide 910 for the proper pressure and measurement path.

According to an embodiment, in operation 880, the electronic device 101 may obtain third information about the current contact pressure value from the external electronic device 102. To that end, according to an embodiment, the electronic device 101 may request the external electronic device 102 to provide the information about the contact pressure value via the first communication circuit 150. However, the third information, according to an embodiment, may be transmitted to the electronic device 101, along with or included in the second information if the external electronic device 102 contacts the user's skin. In other words, if a contact of the external electronic device 102 to the user's skin is detected, the information about the current contact pressure value, according to an embodiment, may be transmitted from the external electronic device 102 to the electronic device 101 even before operations 850 and 860 are performed. According to an embodiment, the information about the contact pressure value may be transmitted to the electronic device 101 automatically without receiving a request from the electronic device 101 if a contact of the external electronic device 102 to the user's skin is detected.

Figure 4D:
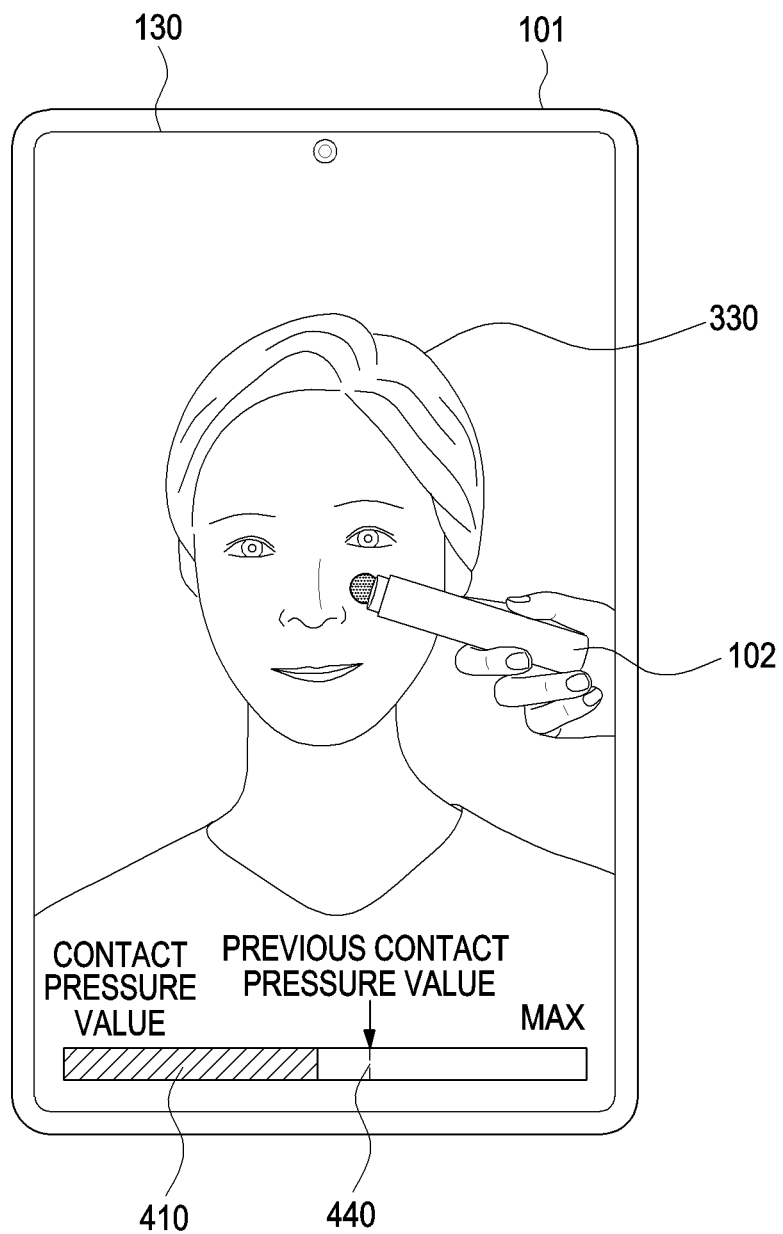

According to an embodiment, the electronic device 101 may provide contact pressure information based on the obtained second information and third information in operation 890. For example, according to an embodiment, the electronic device 101 may output the information 410 (e.g., the relative value or absolute value) about the current contact pressure value via the display 130 as shown in FIG. 4A. According to an embodiment, the electronic device 101 may set a contact pressure value corresponding to the measurement path received from the external electronic device 102, as a recommended contact pressure value and output the information 410 about the current contact pressure value and the information 420 about the recommended contact pressure value via the display 130, as shown in FIG. 4B. According to an embodiment, the electronic device 101 may compare the information about the contact pressure value, corresponding to the measurement path, received from the external electronic device 102 with the obtained contact pressure value, determine whether the current contact pressure value is a proper contact pressure, and output information (e.g., proper) 430 about the result of the determination via the display 130, as shown in FIG. 9B. In this case, according to an embodiment, the electronic device 101 may display the current contact pressure value 410 along with the information (e.g., proper) 430 about the result of determination. Alternatively, the electronic device 101 may display only the information (e.g., proper) 430 about the result of determination. According to an embodiment, as shown in FIG. 4D, the electronic device 101 may output the current contact pressure value measured and contact pressure values for the contacts made during a specific period (e.g., one week) via the display 130. To that end, according to an embodiment, the processor 110 may compute the average contact pressure value for the contacts made to a specific point (e.g., the right cheek) during a specific period (e.g., one week), stored in the memory 120. According to an embodiment, the processor 110 may compare the computed average contact pressure value with the current contact pressure value received from the external electronic device 102. Thus, skin condition measurement or skincare may be performed constantly under the same or similar pressure condition, delivering a reliable result of skin condition measurement or skincare.

According to an embodiment, in operation 870, when the position of the external electronic device 102 is not the correct position (e.g., when the region of the captured front end 210 does not cover the measurement path or any of the edges (or diameter) of the captured front end 210 does not abut the measurement path), the electronic device 101 may provide a notification indicating that the position of the external electronic device 102 is not the correct position. According to an embodiment, the notification may include at least one of a visual notification (e.g., displaying a message), an auditory notification (e.g., outputting a sound message), or a tactile notification (e.g., a vibration).

Figure 10:
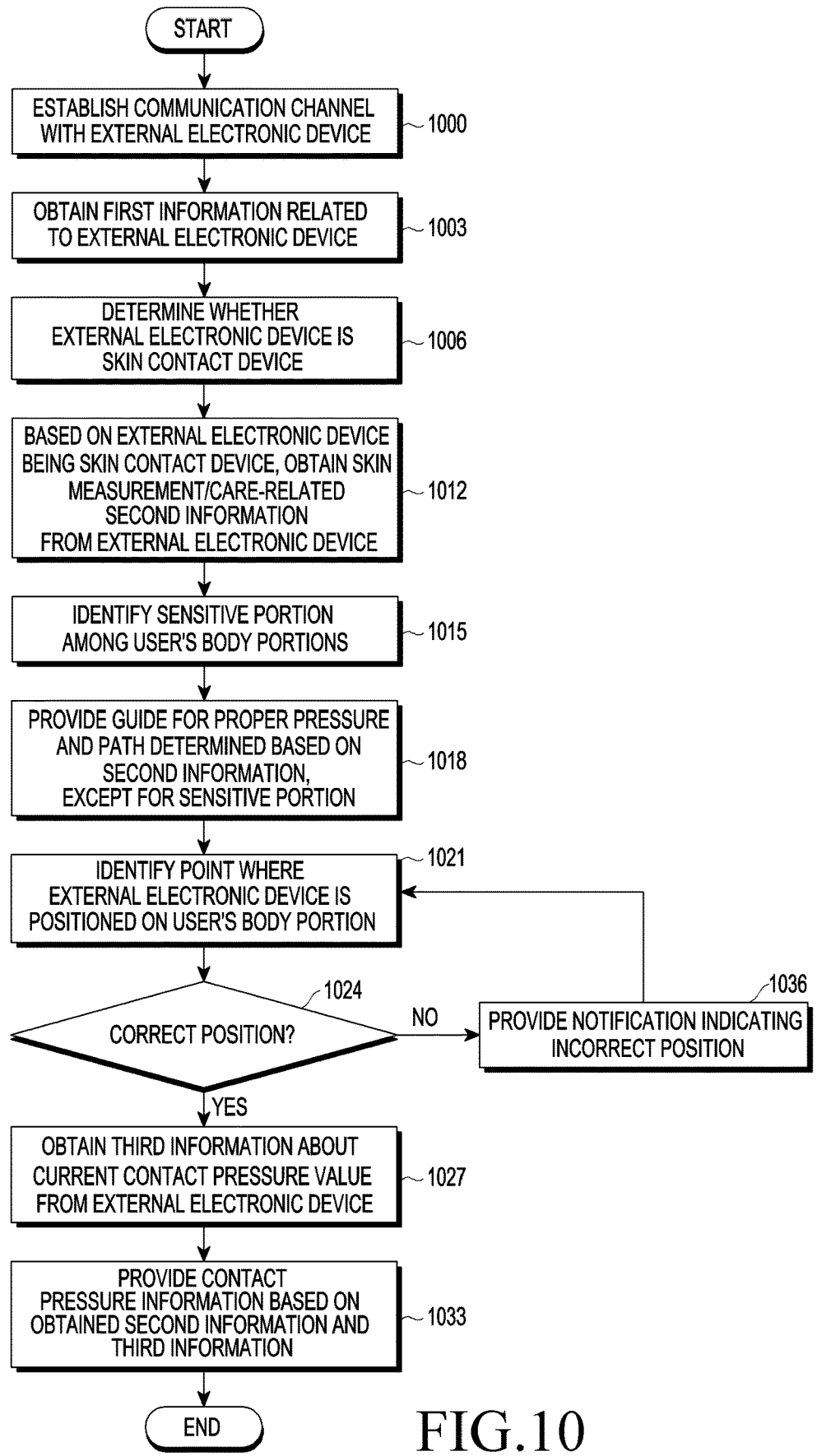
FIG. 10 is a flowchart illustrating an example method in which an electronic device identifies a sensitive skin portion and determines and provides, as a new measurement path, the measurement path except for the sensitive portion, according to various embodiments.
Figure 11A:
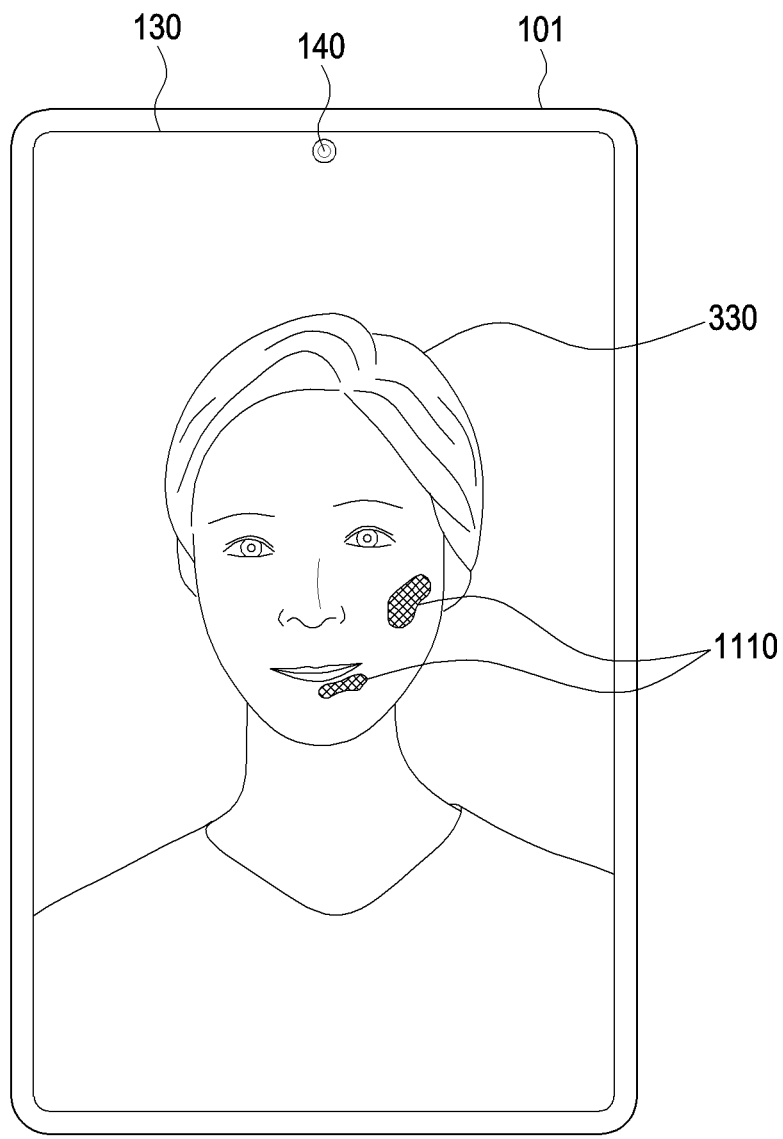
FIGS. 11A, 11B, and 11C are diagrams illustrating an example of the method of FIG. 10 according to various embodiments.
Figure 11B:
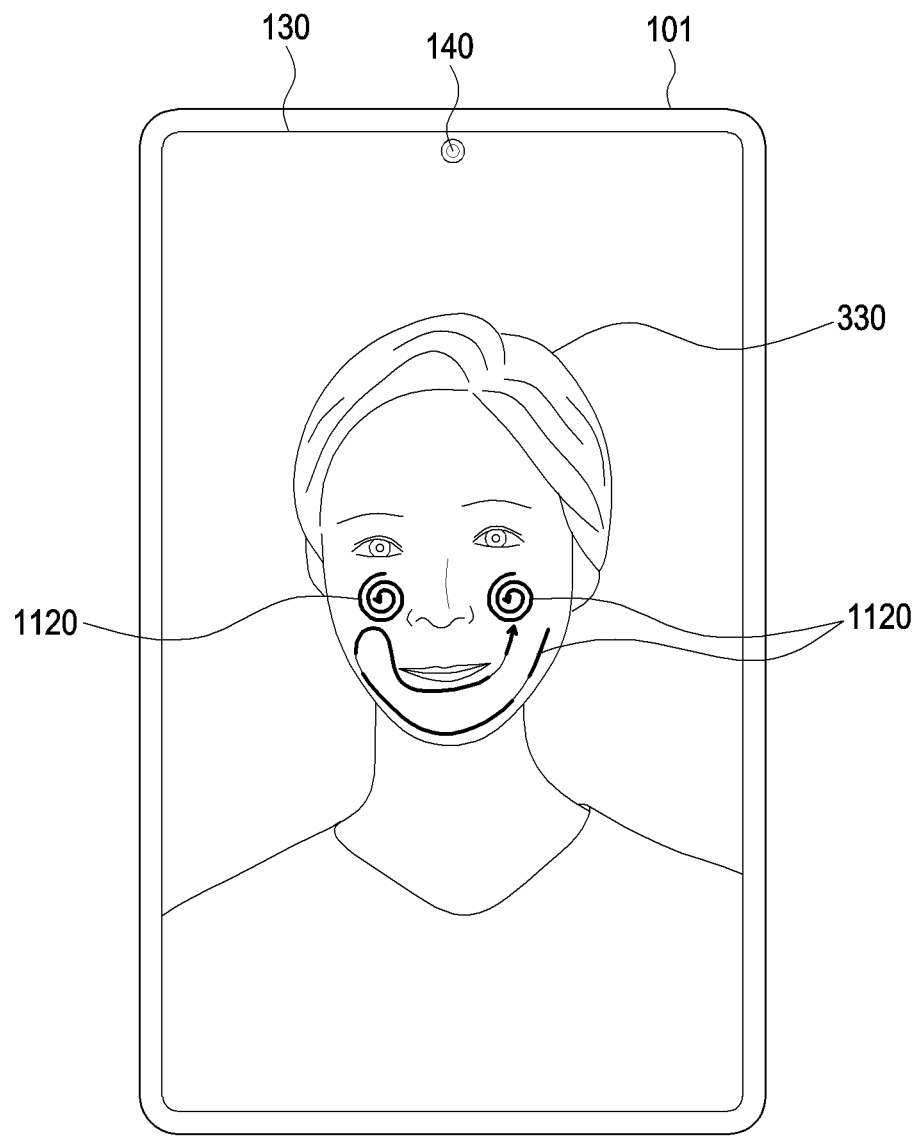
Figure 11C:
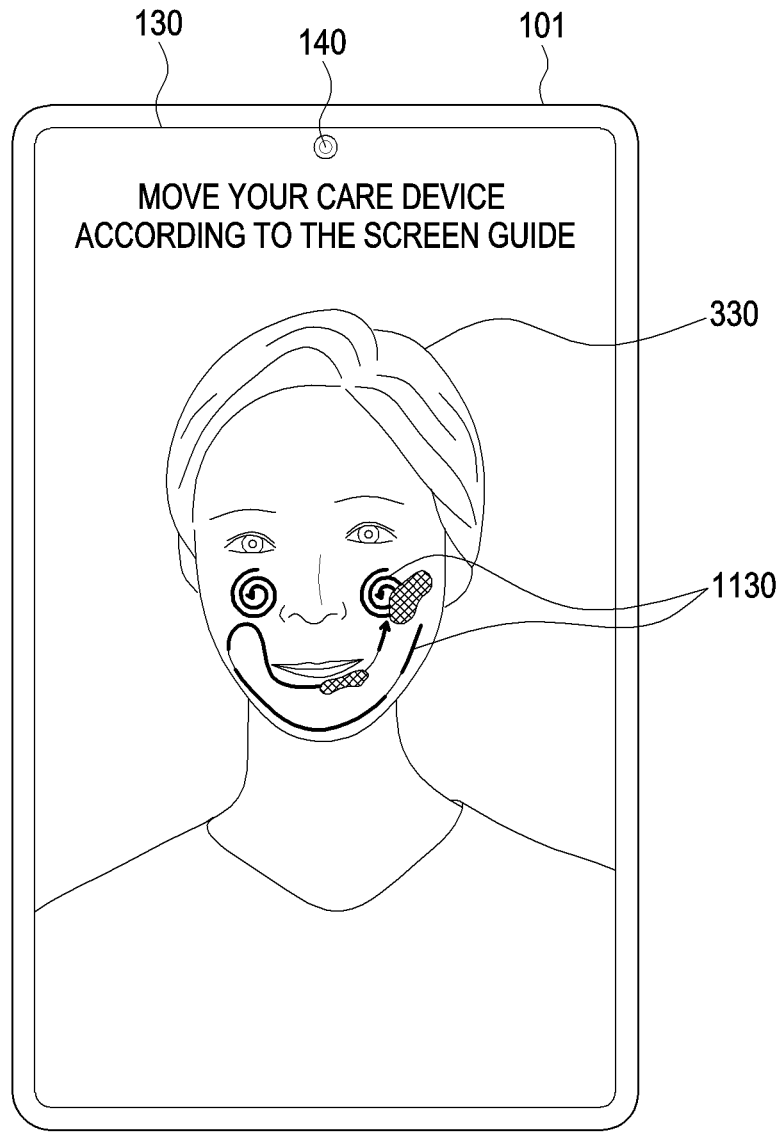

FIG. 10 is a flowchart illustrating an example method in which an electronic device identifies a sensitive skin portion and determines and provides, as a new measurement path, the measurement path except for the sensitive portion, according to various embodiments. FIGS. 11A, 11B, and 11C are diagrams illustrating an example of the method of FIG. 10 according to various embodiments.

Referring to FIG. 10, according to an embodiment, the electronic device 101 may establish a communication channel with the external electronic device 102 in operation 1000. According to an embodiment, the communication channel may include a wired communication channel or a wireless communication channel. According to an embodiment, the wired communication channel may include, e.g., a local area network (LAN) communication channel or a power line communication channel. According to an embodiment, the wireless communication channel may include, e.g., a short-range communication network communication channel, such as Bluetooth, Wi-Fi direct, or infrared data association (IrDA), or a long-range communication network communication channel, such as cellular network, Internet, or computer network (e.g., LAN or wide area network (WAN)).

According to an embodiment, the electronic device 101 may obtain first information related to the external electronic device in operation 1003. According to an embodiment, the first information related to the external electronic device 102 may include at least one of, e.g., information for identifying the type of the external electronic device 102 (e.g., whether the external electronic device 102 is a skin contact device or another type of device), information about the device model name of the external electronic device 102, information about the function supported by the external electronic device 102, or information about the shape of the external electronic device 102.

According to an embodiment, the electronic device 101 may determine whether the external electronic device 102 is a skin contact device in operation 1006. According to an embodiment, the electronic device 101 may identify whether the type of the external electronic device 102 is a skin contact device by identifying the first information (e.g., information for identifying the type of the external electronic device 102) obtained from the external electronic device 102.

According to an embodiment, when the external electronic device 102 is a skin contact device, the electronic device 101 may obtain second information related to skin measurement/care from the external electronic device 102, in operation 1012. According to an embodiment, the second information related to skin measurement/care may include at least one of information about a recommended measurement position (e.g., a specific point) for performing skin condition measurement or skincare, information about per-part (e.g., the left cheek, right cheek, around the chin, and/or the forehead) proper contact pressure value of the user's body portion (e.g., the face), or information about a recommended measurement path, per part, for performing skin condition measurement or skincare.

According to an embodiment, the electronic device 101 may identify a sensitive part 1110 (e.g., a part with skin troubles) of the user's body portion in operation 1015. To identify the sensitive part 1110 (refer to FIG. 11A), according to an embodiment, the electronic device 101 may identify feature points (in other words, a land mark) of the body portion of the user 330. According to an embodiment, the electronic device 101 may identify feature points of the body portion of the user 330 to thereby identify the shape of the body portion and may identify a part (e.g., the sensitive part 1110 of FIG. 11A) with a designated threshold pixel value or more, of the identified body portion shape, as the sensitive part 1110.

According to an embodiment, in operation 1018, the electronic device 101 may provide a guide for a proper pressure and path (e.g., a guide 1130 for a proper pressure and second measurement path as shown in FIG. 11C), except for the measurement path (e.g., a guide 1120 for a proper pressure and first measurement path as shown in FIG. 11B) determined based on the second information (e.g., information about per-part recommended measurement paths for performing skin condition measurement or skincare). According to an embodiment, the electronic device 101 may determine a measurement path (e.g., the guide 1120 for the proper pressure and first measurement path as shown in FIG. 11B) based on the second information and the identified body portion of the user. According to an embodiment, the electronic device 101 may extract only a path, which does not overlap the sensitive part 1110, among the determined measurement paths. According to an embodiment, the electronic device 101 may determine that the extracted path is the guide 1130 for the proper pressure and second measurement path. According to an embodiment, the electronic device 101 may display the guide 1130 for the proper pressure and second measurement path on the display 130. According to an embodiment, the guide 1130 for the proper pressure and second measurement path may be displayed in an augmented reality (AR) manner on the screen where the body portion (e.g., face) of the user 330 is displayed as shown in FIG. 11C but is not limited thereto. According to an embodiment, the electronic device 101 may indirectly indicate a proper pressure for a specific portion by displaying the guide 1130 for the proper pressure and second measurement path in a different thickness. For example, when the thickness of the guide 1130 for the proper pressure and second measurement path is relatively large, the user may be indirectly informed that this portion requires a relatively higher contact pressure. In contrast, when the thickness of the guide 1130 for the proper pressure and measurement path is relatively small, the user may be indirectly informed that this portion requires a relatively lower contact pressure.

According to an embodiment, the electronic device 101 may identify the point where the external electronic device 102 is positioned on the user's body portion in operation 1021. The description made above in connection with operation 250 may apply to the following description.

According to an embodiment, in operation 1024, the electronic device 101 may determine whether the external electronic device 102 is positioned at a correct point. According to an embodiment, the electronic device 101 may determine whether the position of the external electronic device 102 identified by operation 1021 matches the position indicated by the guide 1130 for the proper pressure and second measurement path. For example, according to an embodiment, when the region of the captured front end 210 covers the measurement path or at least part of the edge (or diameter) of the captured front end 210 abuts the measurement path, the electronic device 101 may determine that the identified position of the external electronic device 102 matches the position indicated by the guide 1130 for the proper pressure and second measurement path.

According to an embodiment, in operation 1027, the electronic device 101 may obtain third information about the current contact pressure value from the external electronic device 102. To that end, according to an embodiment, the electronic device 101 may request the external electronic device 102 to provide the information about the contact pressure value via the first communication circuit 150. However, the third information, according to an embodiment, may be transmitted to the electronic device 101, along with or included in the second information if the external electronic device 102 contacts the user's skin. In other words, if a contact of the external electronic device 102 to the user's skin is detected, the information about the current contact pressure value, according to an embodiment, may be transmitted from the external electronic device 102 to the electronic device 101 even before operations 1021 and 1024 are performed. According to an embodiment, the information about the contact pressure value may be transmitted to the electronic device 101 automatically without receiving a request from the electronic device 101 if a contact of the external electronic device 102 to the user's skin is detected.

According to an embodiment, the electronic device 101 may provide contact pressure information based on the obtained second information and third information in operation 1033. For example, according to an embodiment, the electronic device 101 may output the information 410 (e.g., the relative value or absolute value) about the current contact pressure value via the display 130 as shown in FIG. 4A. According to an embodiment, the electronic device 101 may set a contact pressure value corresponding to the measurement path received from the external electronic device 102, as a recommended contact pressure value and output the information 410 about the current contact pressure value and the information 420 about the recommended contact pressure value via the display 130, as shown in FIG. 4B. According to an embodiment, the electronic device 101 may compare the information about the contact pressure value, corresponding to the measurement path, received from the external electronic device 102 with the obtained contact pressure value, determine whether the current contact pressure value is a proper contact pressure, and output information (e.g., proper) 430 about the result of the determination via the display 130, as shown in FIG. 4B. In this case, according to an embodiment, the electronic device 101 may display the current contact pressure value 410 along with the information (e.g., proper) 430 about the result of determination. Alternatively, the electronic device 101 may display only the information (e.g., proper) 430 about the result of determination. According to an embodiment, as shown in FIG. 4D, the electronic device 101 may output the current contact pressure value measured and contact pressure values for the contacts made during a specific period (e.g., one week) via the display 130. To that end, according to an embodiment, the processor 110 may compute the average contact pressure value for the contacts made to a specific point (e.g., the right cheek) during a specific period (e.g., one week), stored in the memory 120. According to an embodiment, the processor 110 may compare the computed average contact pressure value with the current contact pressure value received from the external electronic device 102. Thus, skin condition measurement or skincare may be performed constantly under the same or similar pressure condition, delivering a reliable result of skin condition measurement or skincare.

According to an embodiment, in operation 1036, when the position of the external electronic device 102 is not the correct position (e.g., when the region of the captured front end 210 does not cover the measurement path or any of the edges (or diameter) of the captured front end 210 does not abut the measurement path), the electronic device 101 may provide a notification indicating that the position of the external electronic device 102 is not the correct position. According to an embodiment, the notification may include at least one of a visual notification (e.g., displaying a message), an auditory notification (e.g., outputting a sound message), or a tactile notification (e.g., a vibration).

According to an embodiment, the second information may not include information about the recommended path. In this case, according to an embodiment, the electronic device 101 may generate information about a recommended path and proper pressure according to the type of the external electronic device 102. According to an embodiment, the electronic device 101 may determine that the generated information about the recommended path and proper pressure is the guide 1120 for the proper pressure and first measurement path. According to an embodiment, at least one of the operations of FIG. 10 may be omitted.

Figure 12A:
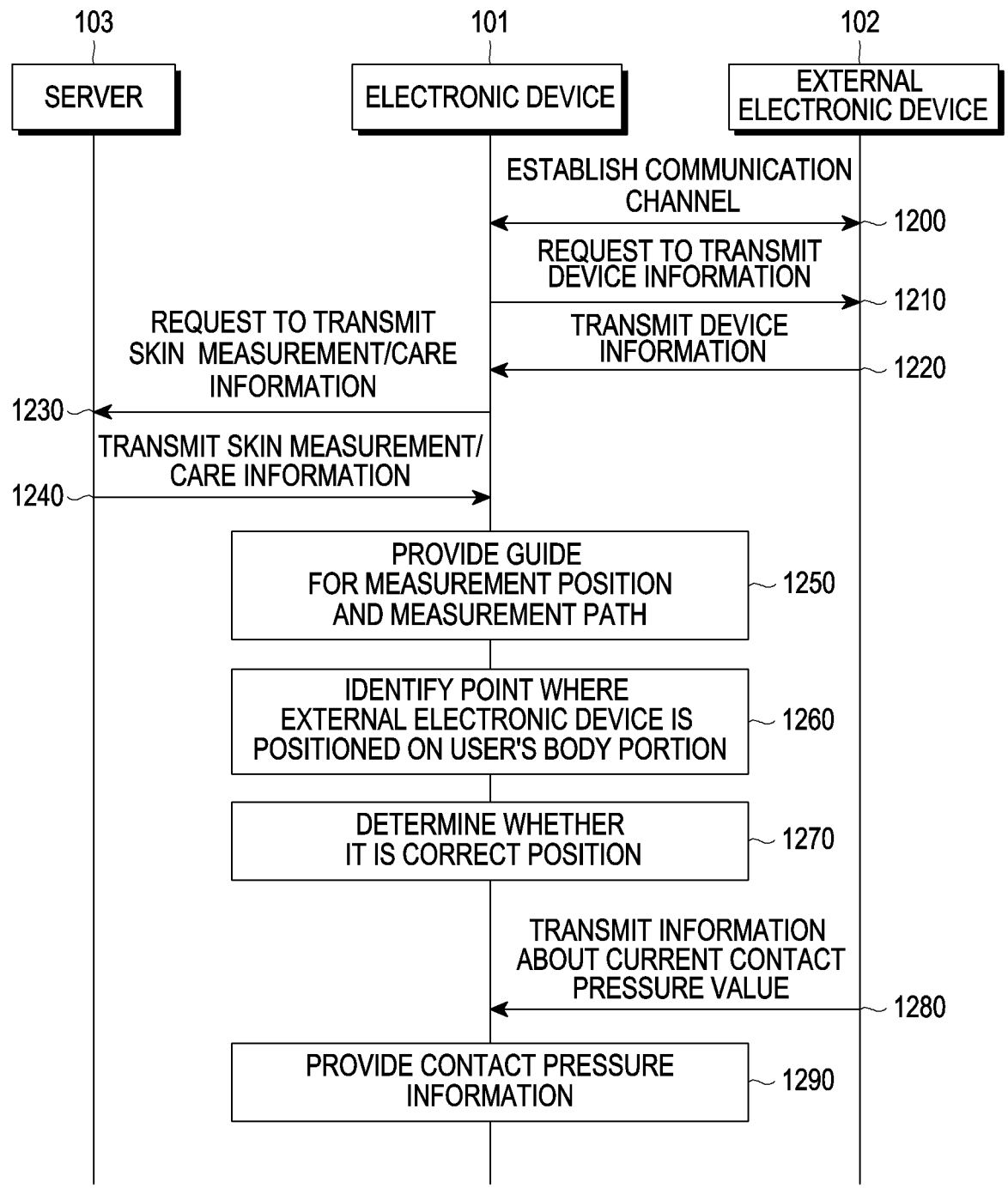
FIGS. 12A and 12B are signal flow diagrams illustrating an example of receiving first information related to an external electronic device from a server, in the embodiments described above in connection with FIGS. 8, 9A, 9B, 10, 11A, 11B and 11C according to various embodiments.
Figure 12B:
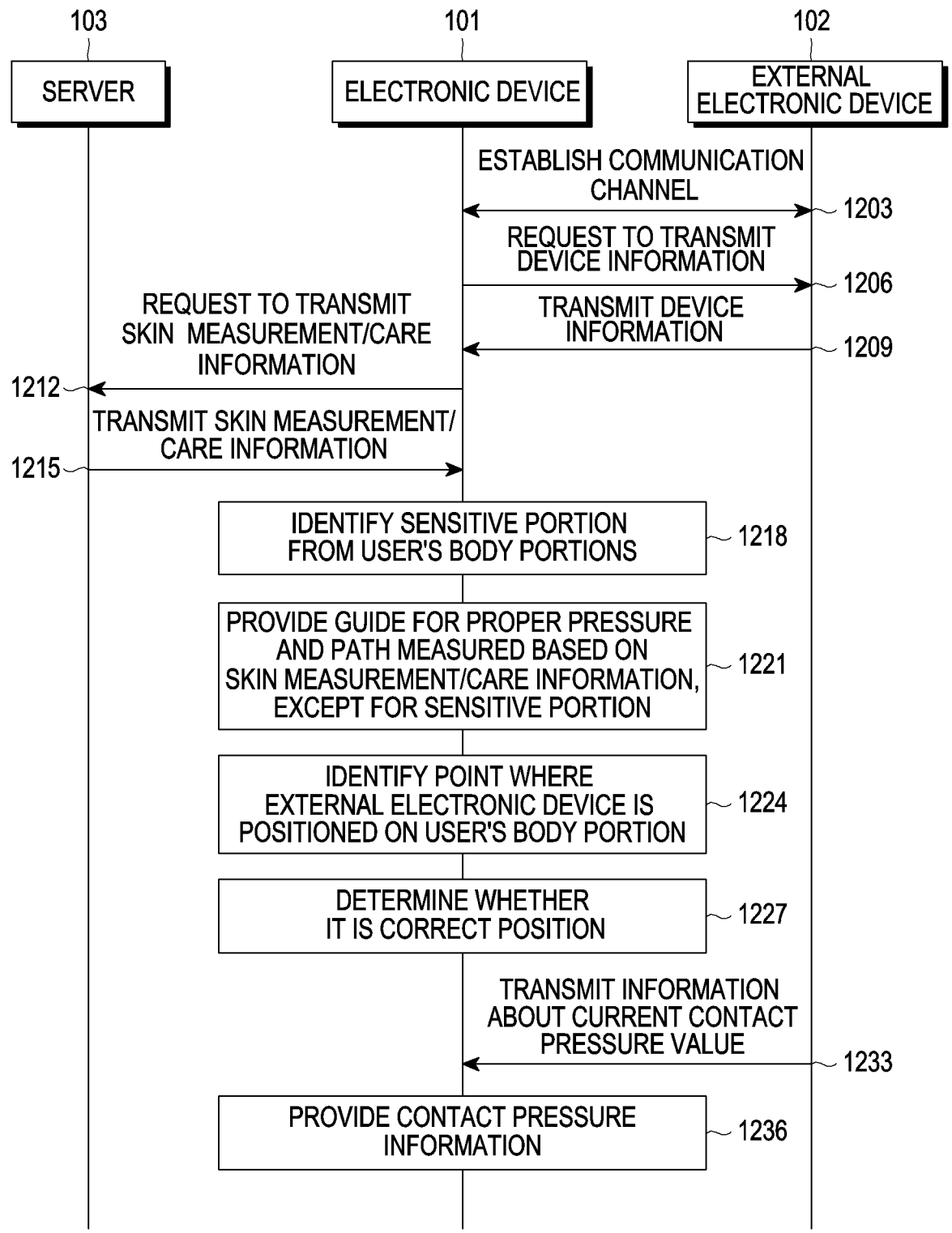

FIGS. 12A and 12B are signal flow diagrams illustrating an example of receiving first information related to an external electronic device 102 from a server 103, in the embodiments described above in connection with FIGS. 8, 9A, 9B, 10, 11A, 11B and 11C according to various embodiments.

Referring to FIG. 12A, according to an embodiment, the electronic device 101 and the external electronic device 102 may establish a communication channel in operation 1200. According to an embodiment, the communication channel may include a wired communication channel or a wireless communication channel. According to an embodiment, the wired communication channel may include, e.g., a local area network (LAN) communication channel or a power line communication channel. According to an embodiment, the wireless communication channel may include, e.g., a short-range communication network communication channel, such as Bluetooth, Wi-Fi direct, or infrared data association (IrDA), or a long-range communication network communication channel, such as cellular network, Internet, or computer network (e.g., LAN or wide area network (WAN)).

According to an embodiment, the electronic device 101 may request the external electronic device 102 to transmit device information of the external electronic device 102 in operation 1210. According to an embodiment, the external electronic device 102 may transmit device information to the electronic device 101 according to the request from the electronic device 101 in operation 1220. According to an embodiment, the device information about the external electronic device 102 may include at least one of, e.g., information for identifying the type of the external electronic device 102 (e.g., whether the external electronic device 102 is a skin contact device or another type of device), information about the device model name of the external electronic device 102, information about the function supported by the external electronic device 102, or information about the shape of the external electronic device 102.

According to an embodiment, in operation 1230, the electronic device 101 may request the server 103 to transmit skin measurement/care information. According to an embodiment, the server 103 may transmit skin measurement/care information to the electronic device 101 according to the request from the electronic device 101 in operation 1240. According to an embodiment, the skin measurement/care information may include at least one of information about a recommended measurement position (e.g., a specific point) for performing skin condition measurement or skincare, information about per-part (e.g., the left cheek, right cheek, around the chin, and/or the forehead) proper contact pressure value of the user's body portion (e.g., the face), or information about a recommended measurement path for performing skin condition measurement or skincare. The description of operations 840, 850, 860, 880, and 890 may be applied to operations 1250, 1260, 1270, 1280 and 1290. What has been described above in connection with FIG. 10 may be applied to the other operations of FIG. 12B than the operation of requesting the server 103 to transmit skin measurement/care information (operation 1212 of FIG. 7B) and the operation of receiving skin measurement/care information from the server 103 at the request (operation 1215 of FIG. 12B), and a detailed description thereof may not be repeated here.

The electronic device according to various embodiments may be one of various types of electronic devices. The electronic devices may include, for example, a portable communication device (e.g., a smart phone), a computer device, a portable multimedia device, a portable medical device, a camera, a wearable device, a home appliance, or the like. According to an embodiment of the disclosure, the electronic device is not limited to the above-listed embodiments.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via a third element.

As used herein, the term "module" may include a unit implemented in hardware, software, or firmware, or any combination thereof, and may interchangeably be used with other terms, for example, "logic," "logic block," "part," or "circuitry". A module may be a single integral component, or a minimum unit or part thereof, adapted to perform one or more functions. For example, according to an embodiment, a module may be implemented in the form of an application-specific integrated circuit (ASIC).

Various embodiments as set forth herein may be implemented as software including one or more instructions that are stored in a storage medium readable by a machine (e.g., the electronic device 101). For example, a processor (e.g., the processor 120) of the machine (e.g., the electronic device 101) may invoke at least one of the one or more instructions stored in the storage medium, and execute it. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program products may be traded as commodities between sellers and buyers. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

As is apparent from the forgoing description, according to various embodiments, it is possible to allow non-professional, ordinary consumers to obtain constant skin condition measurement results or skincare results by providing information related to a proper contact pressure in carrying out skin condition measurement or skincare.

According to various embodiments, it is possible to allow non-professional, ordinary consumers to obtain constant skin condition measurement results or skincare results by providing information about a recommended path and recommended contact pressure for skin condition measurement or skincare.

The effects set forth herein are not limited thereto, and it is apparent to one of ordinary skill in the art that various effects may be disclosed herein.

While the disclosure has been illustrated and described with reference to various example embodiments, it will be understood that the various example embodiments are intended to be illustrative, not limiting. It will be further understood by those skilled in the art that various changes in form and detail may be made without departing from the true spirit and full scope of the disclosure, including the appended claims and their equivalents.

What is claimed is:

1. An electronic device for providing a recommended measurement path for performing skin condition measurement or skincare, the electronic device comprising:
    memory;
    a display;
    a camera;
    a communication circuit; and
    at least one processor,
    wherein the memory stores instructions that, when executed by the at least one processor, cause the electronic device to:
        control the communication circuit to establish a communication channel with an external electronic device including a pressure sensor via the communication circuit;
        display an image including skin of a user and the external electronic device, captured using the camera; and
        obtain contact point information relating to each of a plurality of contact points at which the external electronic device contacts the skin,
    wherein obtaining the contact point information comprises:
    for each respective one of the plurality of contact points:
        obtain contact pressure value information from the pressure sensor of the external electronic device via the established communication channel, the contact pressure value information comprising a contact pressure value at the respective contact point;
        identify, from the image, a part of the skin body with which the external electronic device is in contact at the respective contact point;
        identify, from previously stored information associating parts of the skin and contact pressure values, a specified contact pressure value associated with the identified part of the skin;
        identify a sensitive part of the skin based on a pixel value from the image, the pixel value being equal to or greater than a threshold value;
        determine a recommended measurement path for performing skin condition measurement or skincare, wherein the recommended measurement path does not overlap the sensitive part of the skin; and
        output, via the display, the recommended measurement path and contact pressure-related information related to the contact pressure value at the respective contact point and the specified contact pressure value.

2. The electronic device of claim 1, wherein the instructions cause the electronic device to obtain, as the contact points, points where a front end of the external electronic device is positioned.

3. The electronic device of claim 1, wherein the specified contact pressure value corresponds to a recommended contact pressure value for contact between the external electronic device and the identified part of the skin.

4. The electronic device of claim 1, wherein the instructions cause the electronic device to compare the contact pressure value at the respective contact point and the specified contact pressure value.

5. The electronic device of claim 4, wherein the instructions cause the electronic device to output a result of the comparing.

6. The electronic device of claim 1, wherein the instructions cause the electronic device to:
    output, via the display, guide information, the guide information including a designated position for positioning the external electronic device; and
    determine whether the external electronic device is correctly positioned based on comparing the designated position and a current position of the external electronic device.

7. A method for providing a recommended measurement path for performing skin condition measurement or skincare, the method comprising:
    controlling a communication circuit of an electronic device to establish a communication channel with an external electronic device including a pressure sensor;
    displaying an image including skin of a user and the external electronic device, captured using a camera of the electronic device; and
    obtaining contact point information relating to each of a plurality of contact points at which the external electronic device contacts the skin,
    wherein obtaining the contact point information comprises:
    for each respective one of the plurality of contact points:
        obtaining contact pressure value information from the pressure sensor of the external electronic device via the established communication channel, the contact pressure value information comprising a contact pressure value at the respective contact point;
        identifying, from the image, a part of the skin with which the external electronic device is in contact at the respective contact point;
        identifying, from previously stored information associating parts of the skin and contact pressure values, a specified contact pressure value associated with the identified body part of the skin;
        identifying a sensitive part of the skin based on a pixel value from the image, the pixel value being equal to or greater than a threshold value;
        determining a recommended measurement path for performing skin condition measurement or skincare, wherein the recommended measurement path does not overlap the sensitive part of the skin; and outputting, via a display of the electronic device, the recommended measurement path and contact pressure-related information related to the contact pressure value at the respective contact point and the specified contact pressure value.

8. The method of claim 7, further comprising obtaining, as the contact points, points where a front end of the external electronic device is positioned.

9. The method of claim 7, wherein the specified contact pressure value corresponds to a recommended contact pressure value for contact between the external electronic device and the identified part of the skin.

10. The method of claim 7, further comprising:
comparing the contact pressure value at the respective contact point and the specified contact pressure value.

11. The method of claim 10, further comprising:
outputting a result of the comparing.

12. The method of claim 7, further comprising:
outputting, via the display, guide information, the guide information including a designated position for positioning the external electronic device; and
determining whether the external electronic device is correctly positioned based on comparing the designated position and a current position of the external electronic device.

* * * * *